US 9,150,583 B2

(12) United States Patent
Trieselmann et al.

(10) Patent No.: US 9,150,583 B2
(45) Date of Patent: *Oct. 6, 2015

(54) FURO[3,4-C]QUINOLINE DERIVATIVES, MEDICAMENTS CONTAINING SUCH COMPOUNDS, THEIR USE AND PROCESS FOR THEIR PREPARATION

(75) Inventors: Thomas Trieselmann, Mettenberg (DE); Dieter Hamprecht, Pozzolengo (BS) (DE); Holger Wagner, Mettenberg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/586,977

(22) Filed: Aug. 16, 2012

(65) Prior Publication Data
US 2013/0210850 A1    Aug. 15, 2013

(30) Foreign Application Priority Data
Aug. 17, 2011   (EP) ................................. 11177808

(51) Int. Cl.
*C07D 491/20*    (2006.01)
*A61K 31/4747*   (2006.01)
*A61K 45/06*     (2006.01)

(52) U.S. Cl.
CPC .......... *C07D 491/20* (2013.01); *A61K 31/4747* (2013.01); *A61K 45/06* (2013.01)

(58) Field of Classification Search
USPC ............................................. 546/92; 514/291
See application file for complete search history.

(56) References Cited

U.S. PATENT DOCUMENTS

| | | | |
|---|---|---|---|
| 4,475,407 A | 10/1984 | Kruncos | |
| 4,798,619 A | 1/1989 | Los | |
| 5,932,587 A | 8/1999 | Schmeck et al. | |
| 5,977,136 A | 11/1999 | Di Fabio et al. | |
| 9,029,544 B2 * | 5/2015 | Wagner et al. | 546/89 |
| 2002/0062024 A1 | 5/2002 | Stoltefuss et al. | |
| 2003/0191306 A1 | 10/2003 | Sikorski et al. | |
| 2005/0043341 A1 | 2/2005 | Gielen et al. | |
| 2008/0194609 A1 | 8/2008 | Bischoff et al. | |
| 2008/0255068 A1 | 10/2008 | Bischoff et al. | |
| 2011/0021550 A1 | 1/2011 | Wagner et al. | |
| 2012/0046304 A1 | 2/2012 | Wagner et al. | |
| 2012/0053197 A1 | 3/2012 | Wagner et al. | |
| 2013/0053404 A1 * | 2/2013 | Wagner et al. | 514/256 |
| 2013/0210850 A1 | 8/2013 | Trieselmann et al. | |
| 2013/0210851 A1 | 8/2013 | Ostermeier et al. | |

FOREIGN PATENT DOCUMENTS

| | | | |
|---|---|---|---|
| CA | 2302350 A1 | 3/1999 | |
| EP | 0818197 A1 | 1/1998 | |
| JP | 2008201760 A | 9/2008 | |
| WO | 9002129 A1 | 3/1990 | |
| WO | 9712870 A1 | 4/1997 | |
| WO | 9911629 A1 | 3/1999 | |
| WO | 9914215 A1 | 3/1999 | |
| WO | 03028727 A1 | 4/2003 | |
| WO | 2006024517 A1 | 3/2006 | |
| WO | 2006063828 A1 | 6/2006 | |
| WO | 2006072362 A1 | 7/2006 | |
| WO | 2009109549 A1 | 9/2009 | |
| WO | 2011101424 A1 | 8/2011 | |
| WO | 2012110599 A1 | 8/2012 | |

OTHER PUBLICATIONS

Rano, T.A. et al., "Design and synthesis of potent inhibitors of cholesteryl ester transfer protein (CETP) exploiting a 1,2,3,4-tetrahydroquinoline platform." Biororganic and Medicinal Chemistry Letters, vol. 19, No. 9, May 1, 2009, p. 2456-2460.

Tamura Y. et al., A Synthesis of 5-Amino- and 5-Hydroxy-1-ethyl-1,4-dihydro-4-oxo-3-quinolinecarboxylic acides and their derivatives:. Journal of Heterocyclic Chemistry, vol. 19, 1982, p. 289-296.

Torii, S. et al., "A Facile Synthesis of Polyfunctionally Substituted Phroidines from Ethoxycarbonylmalonaldehyde". Synthesis, Communications. May 1986, p. 400-402.

Vasil'ev, A.N. et al., "Reduction of Alkyl-2-amino-5,6-dialkyl-3-cyanopyridine-4-carboxylates". Russian Journal of Organic Chemistry, vol. 41, No. 2, 2005, p. 288-291.

International Search Report and Written Opinion for PCT/EP2012/065989 mailed Oct. 8, 2012.

* cited by examiner

*Primary Examiner* — John Mabry
*Assistant Examiner* — Daniel Carcanague
(74) *Attorney, Agent, or Firm* — Michael P. Morris; David L. Kershner; Usha R. Patel

(57) ABSTRACT

The present invention relates to compounds defined by formula I (I)

[Chemical structure of furo[3,4-c]quinoline derivative with substituents $R^1$, $R^2$, $R^3$, $R^4$, $R^5$, $R^6$, $R^7$, $R^8$ and OH group]

wherein the variables $R^1$-$R^8$ are defined as in the description, possessing valuable pharmacological activity. Particularly, the compounds are inhibitors of cholesterol ester transfer protein (CETP) and thus are suitable for treatment and prevention of diseases which can be influenced by inhibition of this protein.

16 Claims, No Drawings

FURO[3,4-C]QUINOLINE DERIVATIVES, MEDICAMENTS CONTAINING SUCH COMPOUNDS, THEIR USE AND PROCESS FOR THEIR PREPARATION

FIELD OF APPLICATION OF THE INVENTION

The present invention relates to 1,3,6,7,8,9-hexahydro-furo[3,4-c]quinoline derivatives having the following chemical scaffold which is structurally defined by the formula I

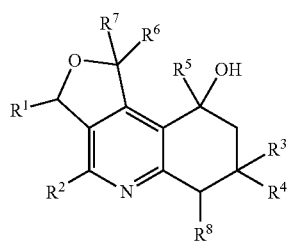

wherein the groups $R^1$ to $R^8$ are as defined hereinafter, including the tautomers, the stereoisomers, the mixtures thereof and the salts thereof. These compounds according to the invention have valuable pharmacological properties and can be used in the pharmaceutical industry for the production of pharmaceutical compositions for use in human and/or veterinary medicine. The invention further relates to pharmaceutical compositions containing one or more compounds according to the invention as well as the use of the compounds according to the invention as medicaments, particularly for preparing pharmaceutical compositions for the treatment and/or prevention of cardiometabolic or cardiovascular disorders. In addition, the invention relates to processes for preparing the compounds and pharmaceutical compositions according to the invention. Further, the invention relates to compounds and pharmaceutical compositions according to the invention for use in methods of inhibiting CETP as well as of treating and/or preventing cardiovascular or related disorders.

KNOWN TECHNICAL BACKGROUND

In the literature, compounds which have an inhibitory effect on the cholesterol ester transfer protein (CETP) are proposed for the treatment of the cardiovascular disorders, in particular hypolipoproteinemia, dyslipidemia, hypertriglyceridemia, hyperlipidemia, hypercholesterolemia and atherosclerosis.

Compounds from various chemical classes are described in the literature as inhibitors of CETP (WO 98/35937, WO 00/017164, WO 05/100298, US2002120011, US2002177708, WO 00/18724). Also, substituted tetrahydroquinoline derivatives (WO 06/063828) have been described, however substituted 1,3,6,7,8,9-hexahydro-furo[3,4-c]quinoline derivatives defined by formula I have not yet been described for the inhibition of CETP.

International Patent Application PCT/EP2011052376 discloses hexahydrofuro[3,4-c]quinoline derivatives, a process for their manufacture and their use in a pharmaceutical composition to treat and/or prevent disorders which can be influenced by inhibiting cholesteryl ester transfer protein (CETP), such as e.g. cardiometabolic or cardiovascular disorders.

AIM OF THE INVENTION

The aim of the present invention is to find new compounds particularly those which have valuable pharmacological properties, especially those which are active with regard to the CETP, such as e.g. 1,3,6,7,8,9-hexahydro-furo[3,4-c]quinoline derivatives. A further aim of the present invention is to discover 1,3,6,7,8,9-hexahydro-furo[3,4-c]quinoline derivatives which have an inhibitory effect on the CETP in vitro and/or in vivo and possess suitable pharmacological and pharmacokinetic properties to use them as medicaments.

A further aim of the present invention is to provide new pharmaceutical compositions which are suitable for the prevention and/or treatment of cardiometabolic or cardiovascular disorders, particularly hypolipoproteinemia, dyslipidemia, hypertriglyceridemia, hyperlipidemia, hypercholesterolemia and atherosclerosis.

Other aims of the present invention will become apparent to the skilled man directly from the foregoing and following remarks.

OBJECT OF THE INVENTION

In a first aspect the present invention relates to compounds which are structurally defined by the formula I

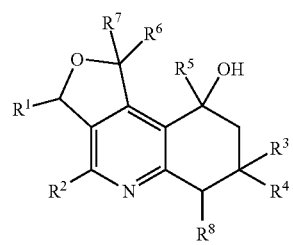

wherein
$R^1$ is a mono- or bicyclic 5- to 10-membered aryl or heteroaryl group, which heteroaryl contains 1 to 4 heteroatoms selected from the group consisting of N, O and S, and which aryl or heteroaryl may optionally be substituted by $R^9$, $R^{10}$ and/or $R^{11}$, in which
$R^9$ is hydrogen, halogen, cyano, 1-4C-alkyl, 2-4C-alkenyl, 3-6C-cycloalkyl, 1-4C-alkoxy, completely or partially fluorine-substituted 1-4C-alkyl, completely or partially fluorine-substituted 1-4C-alkoxy, pentafluorosulfanyl, cyano-1-4C-alkyl, 1-2C-alkyl-3-6C-cycloalkyl, cyano-3-6C-cycloalkyl, 1-2C-alkoxy-1-4C-alkyl, hydroxy-1-4C-alkyl, or 3-(1-2C-alkyl)-oxetan-3-yl,
$R^{10}$ is hydrogen, halogen, cyano, 1-4C-alkyl, 2-4C-alkenyl, 3-6C-cycloalkyl, 1-4C-alkoxy, completely or partially fluorine-substituted 1-4C-alkyl, completely or partially fluorine-substituted 1-4C-alkoxy, cyano-1-4C-alkyl, methyl-3-6C-cycloalkyl, cyano-3-6C-cycloalkyl, methoxy-1-4C-alkyl, hydroxy-1-4C-alkyl, or 3-(1-2C-alkyl)-oxetan-3-yl,
$R^{11}$ is hydrogen or halogen,
or $R^9$ and $R^{10}$ together and with inclusion of the carbon atoms, to which they are attached, form a 5-6C-cycloalkane ring wherein one methylene group may optionally be replaced by oxygen,
which ring, for the case of a 6-membered ring system, may optionally contain a double bond, and/or
which ring may optionally be mono- or disubstituted by methyl, wherein, for the case that both methyl groups are connected to the same carbon, the methyl groups together with the carbon to which they are connected, may optionally form a cyclopropyl ring, $R^2$ is 1-6C-alkyl, 1-3C-perfluoroalkyl, 1-4C-alkoxy-1-4C-alkyl, or 4-7C-cycloalkyl, which 4-7C-cycloalkyl may optionally be mono- or disubstituted by fluorine, hydroxy, methoxy and/or 1-2C-alkyl and in which, for the case of 5-7C-cycloalkyl systems, one methylene group may optionally be replaced by oxygen, $R^3$ and $R^4$ together and with inclusion of the carbon atom, to which they are attached, form a 3-7C-cycloalkane ring, particularly a cyclopropane ring, $R^5$ is hydrogen or 1-4C-alkyl, $R^6$ is 1-4C-alkyl, $R^7$ is hydrogen or 1-4C-alkyl, or $R^6$ and $R^7$ together and with inclusion of the carbon atom, to which they are attached, form a 5-7C-cycloalkane ring wherein one methylene group may optionally be replaced by oxygen, which ring may optionally contain one double bond, and/or which ring may optionally be mono- or disubstituted by fluorine, hydroxyl, 1-2C-alkoxy and/or 1-2C-alkyl, $R^8$ is hydrogen, acetoxy, propionyloxy, methoxy or hydroxyl, the tautomers, the stereoisomers thereof, the mixtures thereof and the salts thereof.

The compounds of formula I according to the invention and the pharmaceutically acceptable salts thereof have valuable pharmacological properties, particularly an inhibitory effect on the cholesteryl ester transfer protein (CETP).

The present invention also relates to the pharmaceutically acceptable salts of the compounds of formula I according to the invention with inorganic or organic acids.

This invention also relates to pharmaceutical compositions, comprising at least one compound of formula I according to the invention or a pharmaceutically acceptable salt thereof, optionally together with one or more inert carriers and/or diluents.

This invention also relates to pharmaceutical compositions comprising or made of (e.g. by combining or mixing of) at least one compound according to the invention (including a pharmaceutically acceptable salt thereof), and one or more excipients, carriers and/or diluents.

This invention also relates to the use of at least one compound of formula I according to the invention or one of the pharmaceutically acceptable salts thereof for preparing a pharmaceutical composition which is suitable for the treatment and/or prevention of diseases, disorders or conditions which can be influenced by inhibiting the cholesteryl ester transfer protein (CETP), such as e.g. those cardiometabolic or cardiovascular disorders mentioned herein.

This invention also relates to the use of at least one compound of formula I according to the invention or one of the pharmaceutically acceptable salts thereof for preparing a pharmaceutical composition which is suitable for the treatment and/or prevention of cardiovascular and related disorders, such as e.g. hypolipoproteinemia, dyslipidemia, hypertriglyceridemia, hyperlipidemia, hypercholesterolemia or atherosclerosis.

This invention also relates to the use of at least one compound of formula I according to the invention or one of the pharmaceutically acceptable salts thereof for preparing a pharmaceutical composition for inhibiting the cholesteryl ester transfer protein (CETP).

This invention also relates to a compound according to the present invention which is suitable for use in therapy and/or prophylaxis, e.g. for the treatment and/or prevention of diseases or conditions which can be influenced by inhibiting the cholesteryl ester transfer protein (CETP), e.g. cardiovascular, cardiometabolic and related disorders, such as e.g. any of those diseases, disorders and conditions mentioned herein.

This invention also relates to a compound according to the present invention which is suitable for inhibiting the cholesteryl ester transfer protein (CETP).

The invention further relates to a process for preparing a pharmaceutical composition according to the invention, comprising incorporating a compound of formula I according to the invention or one of the pharmaceutically acceptable salts thereof in one or more inert carriers and/or diluents preferably by a non-chemical method.

The present invention also relates to a method for treating and/or preventing a disease or condition which can be influenced by inhibiting the cholesteryl ester transfer protein (CETP), e.g. a cardiovascular, cardiometabolic or related disorder, such as e.g. any of those diseases and conditions mentioned herein, in a mammalian (particularly human) patient in need thereof comprising administering to said patient a therapeutically effective amount of a compound of formula I according to the invention or one of the pharmaceutically acceptable salts thereof.

The present invention also relates to a pharmaceutical compound or composition according to this invention for use in a method of treating and/or preventing a condition which can be influenced by inhibiting the cholesteryl ester transfer protein (CETP), e.g. a cardiovascular, cardiometabolic or related disorder, such as e.g. any of those diseases and conditions mentioned herein, said method comprising administration of said compound or composition, optionally alone or in combination (such as e.g. separately, sequentially, simultaneously, concurrently or chronologically staggered) with one or more other therapeutic agents, such as e.g. selected from those mentioned herein.

The present invention also relates to a compound of formula I according to this invention or a pharmaceutically acceptable salt thereof for use in a method of treating and/or preventing a cardiovascular, cardiometabolic or related disorder selected from atherosclerosis, dyslipidemia (e.g. mixed dyslipidemia), hyperbeta-lipoproteinemia, hypoalpha-lipoproteinemia, hypercholesterolemia, hypertriglyceridemia, hyperlipidemia, hypolipoproteinemia, hyperlipoproteinemia, hypo-HDL cholesterolemia, hyper-LDL cholesterolemia, familial hypercholesterolemia, peripheral vascular disease, hypertension, endothelial dysfunction, angina, ischemia, cardiac ischemia, stroke, myocardial infarction, reperfusion injury, angioplastic restenosis, arteriosclerosis, coronary heart disease, coronary artery disease, coronary vascular disease or congestive heart failure, vascular complications of diabetes, insulin resistance, obesity, metabolic syndrome, diabetes (especially type 2 diabetes meliitus) or endotoxemia, said method comprising administration of said compound or pharmaceutically acceptable salt thereof, optionally in monotherapy or in combination therapy (such as e.g. separately, sequentially, simultaneously, concurrently or chronologically staggered) with one or more other therapeutic agents, such as e.g. selected from those mentioned herein, such as e.g. a HMG-CoA reductase inhibitor (e.g. a statin).

The present invention also relates to a compound of formula I according to this invention or a pharmaceutically acceptable salt thereof for use in a method of increasing patient's levels of HDL cholesterol and/or decreasing patient's levels of VLDL cholesterol and/or of LDL cholesterol, optionally in combination with one or more other therapeutic agents, such as e.g. selected from those mentioned herein, such as e.g. a HMG-CoA reductase inhibitor (e.g. a statin).

The present invention also relates to a compound of formula I according to this invention or a pharmaceutically acceptable salt thereof for use in a method of primary or secondary prevention of cardiovascular diseases, particularly major cardiovascular events, optionally in combination with one or more other therapeutic agents, such as e.g. selected from those mentioned herein, such as e.g. a HMG-CoA reductase inhibitor (e.g. a statin).

The present invention also relates to processes and intermediates for preparing the compounds of general formula I according to the invention (see processes a and b in general synthesis section), the tautomers, the stereoisomers thereof, the mixtures thereof and the salts thereof.

Among the synthesis processes according to this invention, especially noteworthy is the process for preparing a compound of the formula VII, e.g. as an intermediate in the synthesis of compounds of formula I, from compounds of formula IX and VIII

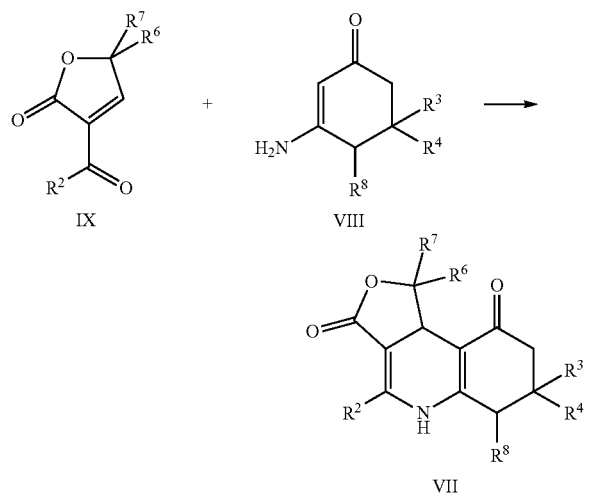

wherein the variables $R^2$, $R^3$, $R^4$, $R^6$ and $R^7$ are as defined hereinbefore and hereinafter and $R^8$ denotes hydrogen, particularly said process comprising reacting a compound of formula IX with a compound of formula VIII, e.g. either neat under reduced pressure at temperatures between 150° C. and 250° C. or in a suitable solvent such as e.g. acetic acid at temperatures between 100° C. and 150° C., to yield the compounds of formula VII.

Among the intermediates according to this invention, especially noteworthy is the use of intermediate of formula VI in the synthesis of compounds of formula I

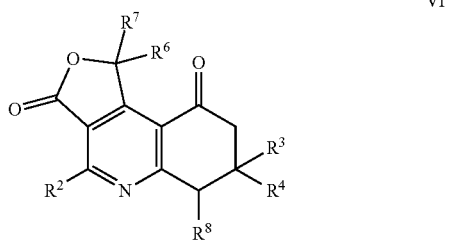

wherein the variables $R^2$, $R^3$, $R^4$, $R^6$ and $R^7$ are as defined hereinbefore and hereinafter and $R^8$ denotes hydrogen.

Other aspects of the present invention become apparent from the description hereinbefore and hereinafter (including the examples) as well as the claims.

DETAILED DESCRIPTION OF THE INVENTION

Unless otherwise stated, the groups, residues, and substituents, particularly $R^1$, $R^2$, $R^3$, $R^4$, $R^5$, $R^6$, $R^7$, $R^8$, $R^9$, $R^{10}$ and $R^{11}$ are defined as above and hereinafter. If residues, substituents, or groups occur several times in a compound they may have the same or different meanings. Some preferred meanings of groups and substituents of the compounds according to the invention will be given hereinafter.

Preferred embodiments of the invention are characterized by the following definitions:

a) Definitions ($a^i$) for $R^1$ in the order of preference, ascending from preferably ($a^1$) to more preferably ($a^2$) up to most preferably ($a^5$):

($a^1$): Preferably, $R^1$ denotes thiophenyl, thiazolyl, phenyl, pyridyl, pyrimidinyl, pyridazinyl or pyrazinyl, each of which substituted by R9, R10 and/or R11, or 1,1-dimethyl-1,3-dihydroisobenzofuran-5-yl, 3'H-spiro[cyclopropane-1,1'-isobenzofuran]-5'-yl, 3,3-dimethyl-2,3-dihydrobenzofuran-6-yl or 2H-spiro[benzofuran-3,1'-cyclopropane]-6-yl, in which $R^9$ is hydrogen, halogen, cyano, 1-4C-alkyl, 2-4C-alkenyl, 3-4C-cycloalkyl, 1-3C-alkoxy, completely or predominantly fluorine-substituted 1-3C-alkyl, completely or predominantly fluorine-substituted 1-3C-alkoxy, pentafluorosulfanyl, cyano-1-3C-alkyl, 1-2C-alkyl-3-4C-cycloalkyl, cyano-3-4C-cycloalkyl, 1-2C-alkoxy-1-3C-alkyl, hydroxy-1-3C-alkyl, or 3-(1-2C-alkyl)-oxetan-3-yl, $R^{10}$ is hydrogen, halogen, cyano, 1-4C-alkyl, 1-3C-alkoxy, completely or predominantly fluorine-substituted 1-3C-alkyl, completely or predominantly fluorine-substituted 1-3C-alkoxy, cyano-1-3C-alkyl, or methoxy-1-3C-alkyl, $R^{11}$ is hydrogen or halogen.

($a^2$): More preferably, $R^1$ denotes 2-($R^9$)-3-($R^{10}$)-thiophen-5-yl, 5-($R^9$)-4-($R^{10}$)-thiazol-2-yl, 1-($R^{10}$)-2-($R^9$)-3-($R^{11}$)-benzene-5-yl, 1-($R^{10}$)-2-($R^9$)-4-($R^{11}$)-benzene-5-yl, 5-($R^9$)-4-($R^{10}$)-pyridine-2-yl, 2-($R^9$)-3-($R^{10}$)-pyridine-5-yl, 5-($R^9$)-3-($R^{10}$)-pyridine-2-yl, 5-($R^9$)-4-($R^{10}$)-pyrimidine-2-yl, 2-($R^9$)-pyrimidine-5-yl, 3-($R^9$)-4-($R^{10}$)-pyridazine-6-yl, 2-($R^9$)-3-($R^{10}$)-pyrazine-5-yl, 1,1-dimethyl-1,3-dihydroisobenzofuran-5-yl, 3'H-spiro[cyclopropane-1,1'-isobenzofuran]-5'-yl, 3,3-dimethyl-2,3-dihydrobenzofuran-6-yl or 2H-spiro[benzofuran-3,1'-cyclopropane]-6-yl, in which $R^9$ is hydrogen, halogen, cyano, isopropyl, isobutyl, tert.-butyl, isopropenyl, cyclopropyl, cyclobutyl, methoxy, ethoxy, isopropoxy, tert.-butoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 1-methoxy-ethan-1-yl, 2-methoxy-propan-2-yl, 1-hydroxy-ethan-1-yl, 2-hydroxy-propan-2-yl, or 3-(1-2C-alkyl)-oxetan-3-yl, $R^{10}$ is hydrogen, halogen, cyano, methyl, ethyl, isopropyl, tert.-butyl, methoxy, trifluoromethyl, trifluoromethoxy, or methoxymethyl, $R^{11}$ is hydrogen, fluorine or chlorine.

($a^3$): Even more preferably, $R^1$ denotes 2-($R^9$)-thiophen-5-yl, 1-($R^9$)-2-($R^{10}$)-benzene-4-yl, 1-($R^9$)-3-($R^{10}$)-benzene-4-yl, 4-($R^9$)-benzene-1-yl, 3-tert.-butylphenyl, 3-trifluoromethylphenyl, 1,2,3-trifluoro-benzene-5-yl, 1,3-difluoro-benzene-5-yl, 5-($R^9$)-pyridine-2-yl, 2-($R^9$)-pyridine-5-yl, 5-($R^9$)-3-($R^{10}$)-pyridine-2-yl, 2-($R^9$)-pyrimidine-5-yl, 5-($R^9$)-4-($R^{10}$)-thiazol-2-yl, 1,1-dimethyl-1,3-dihydroisobenzofuran-5-yl or 3,3-dimethyl-2,3-dihydrobenzofuran-6-yl, in which $R^9$ is fluorine, chlorine, bromine, cyano, isopropyl, isobutyl, isopropenyl, tert.-butyl, cyclopropyl, cyclobutyl, methoxy, ethoxy, isopropoxy, tert.-butoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 2-methoxy-propan-2-yl, 2-hydroxy-propan-2-yl, or 3-methyl-oxetan-3-yl, $R^{10}$ is hydrogen, methyl, cyano, methoxy, fluorine or chlorine.

($a^4$): Yet even more preferably, $R^1$ denotes 4-trifluoromethylphenyl, 3-trifluoromethylphenyl, 4-(1,1-difluor-ethan-1-yl)-phenyl, 4-methylphenyl, 4-isopropylphenyl, 4-isobutylphenyl, 4-tert.-butylphenyl, 3-tert.-butylphenyl, 4-isopropenylphenyl, 4-cyanophenyl, 4-fluorophenyl, 3,5-difluorophenyl, 4-chlorophenyl, 4-methoxyphenyl, 4-isopropoxyphenyl, 4-tert.-butoxyphenyl, 4-trifluoromethoxyphenyl, 4-pentafluorosulfanylphenyl, 4-pentafluoroethylphenyl, 2-trifluoromethyl-pyridin-5-yl, 5-trifluoromethyl-pyridin-2-yl, 3-fluoro-4-trifluoromethyl-phenyl, 2-fluoro-4-trifluoromethylphenyl, 3-fluoro-5-trifluoromethyl-pyridin-2-yl, 3-cyano-4-trifluoromethylphenyl, 3-methoxy-4-trifluoromethylphenyl, 4-(2-cyano-propan-2-yl)-phenyl, 4-(2-hydroxy-propan-2-yl)-phenyl, 4-cyclopropylphenyl, 4-(1-methylcyclopropyl-1-yl)-phenyl, 4-(1-cyanocyclopropyl-1-yl)-phenyl, 2-trifluormethyl-thiophen-5-yl, 4-(3-methyl-oxetan-3-yl)-phenyl, 5-tert.-butyl-4-methyl-thiazol-2-yl or 2-tert.-butyl-pyrimidin-5-yl.

($a^5$): Most preferably, $R^1$ denotes 4-trifluoromethylphenyl, 4-tert.-butylphenyl, 4-pentafluorosulfanylphenyl, 4-pentafluoroethylphenyl, 2-trifluoromethyl-pyridin-5-yl, 3-fluoro-4-trifluoromethyl-phenyl, 2-fluoro-4-trifluoromethylphenyl, 3-cyano-4-trifluoromethylphenyl or 3-methoxy-4-trifluoromethylphenyl.

b) Definitions ($b^i$) for $R^2$ in the order of preference, ascending from preferably ($b^1$) to more preferably ($b^2$) up to most preferably ($b^6$):

($b^1$): Preferably, $R^2$ denotes 1-5C-alkyl, trifluormethyl, pentafluorethyl, 1-3C-alkoxy-1-2C-alkyl, 1-3C-alkoxy-3C-alkyl or 4-7C-cycloalkyl, which 4-7C-cycloalkyl may optionally be mono- or disubstituted by fluorine, hydroxy, methoxy and/or methyl and in which, for the case of 5-7C-cycloalkyl systems, one methylene group may optionally be replaced by oxygen.

($b^2$): More preferably, $R^2$ denotes 1-5C-alkyl, trifluormethyl, 1-3C-alkoxy-1-2C-alkyl, 1-3C-alkoxy-3C-alkyl, cyclobutyl, methylcyclobutyl, dimethylcyclobutyl, cyclopentyl, methylcyclopentyl, cyclohexyl, methylcyclohexyl, dimethylcyclohexyl, fluorcyclohexyl, difluorcyclohexyl, hydroxycyclohexyl, methoxycyclohexyl, tetrahydrofuranyl or tetrahydropyranyl.

($b^3$): Even more preferably, $R^2$ denotes ethyl, isopropyl, 2-butyl, isobutyl, tert.-butyl, 3-pentyl, cyclobutyl, cyclopentyl, cyclohexyl, methoxymethyl, 1-methoxyethyl, 2-methoxy-propan-2-yl, tetrahydrofuran-2-yl, tetrahydrofuran-3-yl, tetrahydropyran-4-yl, tetrahydropyran-3-yl or tetrahydropyran-2-yl.

($b^4$): Yet even more preferably, $R^2$ denotes ethyl, isopropyl, tert.-butyl, methoxymethyl, 1-methoxyethyl, 2-methoxy-propan-2-yl, cyclobutyl, cyclopentyl or tetrahydropyran-4-yl.

($b^5$): Still yet even more preferably, $R^2$ denotes isopropyl, tert.-butyl or tetrahydropyran-4-yl.

($b^6$): Most preferably, $R^2$ denotes isopropyl.

c) Definitions ($c^i$) for $R^3$ and $R^4$ in the order of preference, ascending from preferably ($c^1$) to more preferably ($c^2$) up to most preferably ($c^3$):

($c^1$) Preferably, $R^3$ and $R^4$ together and with inclusion of the carbon atom, to which they are attached, form a cyclopropane, cyclobutane or cyclopentane ring.

($c^2$) More preferably, $R^3$ and $R^4$ together and with inclusion of the carbon atom, to which they are attached, form a cyclopropane or cyclobutane ring.

($c^3$) Most preferably, $R^3$ and $R^4$ together and with inclusion of the carbon atom, to which they are attached, form a cyclopropane ring.

d) Definitions ($d^i$) for $R^5$ in the order of preference, ascending from preferably ($d^1$) to more preferably ($d^2$) up to most preferably ($d^3$):

($d^1$) Preferably, $R^5$ denotes hydrogen, methyl or ethyl.

($d^2$) More preferably, $R^5$ denotes hydrogen or methyl.

($d^3$) Most preferably, $R^5$ denotes hydrogen.

e) Definitions ($e^i$) for $R^6$ and $R^7$ in the order of preference, ascending from preferably ($e^1$) to more preferably ($e^2$) up to most preferably ($e^5$):

($e^1$) Preferably, $R^6$ denotes methyl, ethyl, propyl or isopropyl and $R^7$ denotes hydrogen, methyl or ethyl, or $R^6$ and $R^7$ together and with inclusion of the carbon atom, to which they are attached, form a 5-6C-cycloalkane ring wherein one methylene group may optionally be replaced by oxygen, which ring may optionally contain one double bond, and/or which ring may optionally be mono- or disubstituted by fluorine, hydroxyl, 1-2C-alkoxy and/or 1-2C-alkyl.

($e^2$) More preferably, $R^6$ denotes methyl, ethyl, propyl or isopropyl and $R^7$ denotes hydrogen, methyl or ethyl, or $R^6$ and $R^7$ together and with inclusion of the carbon atom, to which they are attached, form a cyclopentane ring, cyclopentene ring, cyclohexane ring or tetrahydropyrane ring.

($e^3$) Even more preferably, $R^6$ and $R^7$ independently denote methyl or ethyl, or $R^6$ and $R^7$ together and with inclusion of the carbon atom, to which they are attached, form a cyclopentane ring, cyclopent-2-ene-1,1-diyl ring, cyclohexane ring, 4,4-difluorocyclohexane-1,1-diyl ring or tetrahydropyrane-4,4-diyl ring.

($e^4$) Yet even more preferably, $R^6$ denotes methyl and $R^7$ denotes methyl, or $R^6$ and $R^7$ together and with inclusion of the carbon atom, to which they are attached, form a cyclopentane ring, cyclopent-2-ene-1,1-diyl ring, cyclohexane ring or tetrahydropyrane-4,4-diyl ring.

($e^5$) Most preferably, $R^6$ and $R^7$ together and with inclusion of the carbon atom, to which they are attached, form a tetrahydropyrane-4,4-diyl ring.

f) Definitions ($f^i$) for $R^8$ in the order of preference, ascending from preferably ($f^1$) to more preferably ($f^2$) up to most preferably ($f^3$):

($f^1$) Preferably, $R^8$ denotes hydrogen, acetoxy or hydroxy.

($f^2$) More preferably, $R^8$ denotes hydrogen or hydroxy.

($f^3$) Most preferably, $R^8$ denotes hydrogen.

Any and each of the above definitions a) ($a^1$) to f) ($f^1$) may be combined with one another.

Each $a^i$, $b^i$, $c^i$, $d^i$, $e^i$, $f^i$ of a) to f) represents a characterized, individual embodiment of the corresponding substituent as described above. Thus given the above definitions, preferred individual embodiments of the compounds of formula I according to the invention (including the tautomers, the stereoisomers, the mixtures, and the salts thereof) are fully characterized by the term ($a^i b^i c^i d^i e^i f^i$), wherein for each index i an individual figure is given and i ranges from 1 to the highest number given above; index 0 for each letter refers to the individual embodiment given at the outset of the part "Object of the invention". Indices i vary independently from each other. All individual embodiments described by the term in parantheses with full permutation of the indices i, including i equals 0, referring to the definitions above, shall be comprised by the present invention.

The following Table 1 shows, exemplarily and in the order of increasing preference from the first line to the last line, such embodiments E-1 to E-16 of the compounds according to the invention that are considered preferred. This means that embodiment E-16, represented by the entries in the last row of Table 1, is the most preferred embodiment.

TABLE 1

Preferred individual embodiments E-1 to E-16 of the invention

| | $R^1$ | $R^2$ | $R^3/R^4$ | $R^5$ | $R^6/R^7$ | $R^8$ |
|---|---|---|---|---|---|---|
| E-1 | $a^1$ | $b^1$ | $c^1$ | $d^1$ | $e^1$ | $f^1$ |
| E-2 | $a^1$ | $b^1$ | $c^1$ | $d^2$ | $e^1$ | $f^1$ |
| E-3 | $a^2$ | $b^1$ | $c^1$ | $d^2$ | $e^1$ | $f^1$ |
| E-4 | $a^2$ | $b^2$ | $c^1$ | $d^2$ | $e^1$ | $f^2$ |
| E-5 | $a^2$ | $b^2$ | $c^1$ | $d^2$ | $e^2$ | $f^1$ |
| E-6 | $a^2$ | $b^3$ | $c^2$ | $d^3$ | $e^2$ | $f^1$ |
| E-7 | $a^3$ | $b^3$ | $c^2$ | $d^3$ | $e^2$ | $f^2$ |
| E-8 | $a^3$ | $b^3$ | $c^2$ | $d^3$ | $e^3$ | $f^2$ |
| E-9 | $a^3$ | $b^4$ | $c^2$ | $d^3$ | $e^3$ | $f^2$ |
| E-10 | $a^4$ | $b^4$ | $c^2$ | $d^3$ | $e^3$ | $f^1$ |
| E-11 | $a^4$ | $b^4$ | $c^2$ | $d^3$ | $e^4$ | $f^2$ |
| E-12 | $a^4$ | $b^4$ | $c^3$ | $d^3$ | $e^4$ | $f^3$ |
| E-13 | $a^5$ | $b^5$ | $c^3$ | $d^3$ | $e^5$ | $f^2$ |
| E-14 | $a^5$ | $b^5$ | $c^3$ | $d^3$ | $e^5$ | $f^3$ |
| E-15 | $a^5$ | $b^6$ | $c^3$ | $d^3$ | $e^5$ | $f^2$ |
| E-16 | $a^5$ | $b^6$ | $c^3$ | $d^3$ | $e^5$ | $f^3$ | each including the tautomers, the stereoisomers, the mixtures, and the salts thereof.

Another preferred embodiment of the compounds of formula I according to this invention refers to compounds of formula I*

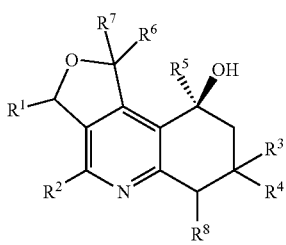

(I*)

wherein the variables $R^1$-$R^8$ are defined as hereinbefore and hereinafter, their tautomers, their stereoisomers, mixtures thereof, and the salts thereof.

This embodiment also includes compounds of formula I*, wherein the variables $R^1$-$R^8$ are selected from above definitions a) ($a^1$) to f) ($f^3$), their tautomers, their stereoisomers, mixtures thereof, and the salts thereof.

Particularly, this embodiment refers to compounds of formula I* as defined by the embodiment E-1, E-2, E-3, E-4, E-5, E-6, E-7, E-8, E-9, E-10, E-11, E-12, E-13, E-14, E-15 or E-16 in Table 1, and the salts thereof.

An embodiment of the compounds of formula I according to this invention refers to compounds of formula I**

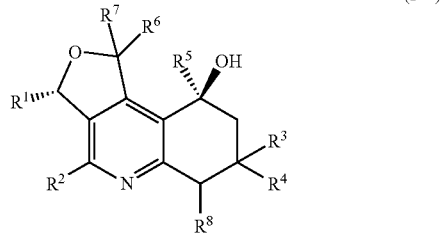

(I**)

wherein the variables $R^1$-$R^8$ are defined as hereinbefore and hereinafter, their tautomers, their stereoisomers, mixtures thereof, and the salts thereof.

This embodiment also includes compounds of formula I**, wherein the variables $R^1$-$R^8$ are selected from above definitions a) ($a^1$) to f) ($f^3$), their tautomers, their stereoisomers, mixtures thereof, and the salts thereof.

Particularly, this embodiment refers to compounds of formula I** as defined by the embodiment E-1, E-2, E-3, E-4, E-5, E-6, E-7, E-8, E-9, E-10, E-11, E-12, E-13, E-14, E-15 or E-16 in Table 1, and the salts thereof.

A further preferred embodiment of the compounds of formula I according to this invention refers to compounds of formula I***

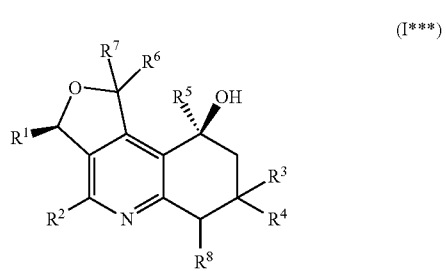

(I***)

wherein the variables $R^1$-$R^8$ are defined as hereinbefore and hereinafter, their tautomers, their stereoisomers, mixtures thereof, and the salts thereof.

This embodiment also includes compounds of formula I***, wherein the variables $R^1$-$R^8$ are selected from above definitions a) ($a^1$) to f) ($f^3$), their tautomers, their stereoisomers, mixtures thereof, and the salts thereof.

Particularly, this embodiment refers to compounds of formula I*** as defined by the embodiment E-1, E-2, E-3, E-4, E-5, E-6, E-7, E-8, E-9, E-10, E-11, E-12, E-13, E-14, E-15 or E-16 in Table 1, and the salts thereof.

A further embodiment of the compounds of formula I according to this invention refers to compounds of formula I****

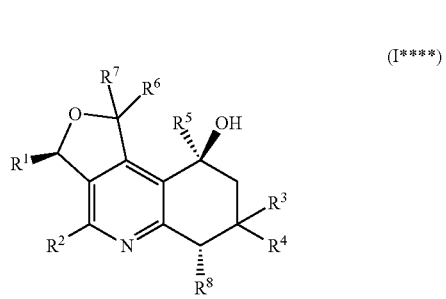

(I****)

wherein the variables R¹-R⁸ are defined as hereinbefore and hereinafter, their tautomers, their stereoisomers, mixtures thereof, and the salts thereof.

This embodiment also includes compounds of formula I****, wherein the variables R¹-R⁸ are selected from above definitions a) (a¹) to f) (f³), their tautomers, their stereoisomers, mixtures thereof, and the salts thereof.

Particularly, this embodiment refers to compounds of formula I**** as defined by the embodiment E-1, E-2, E-3, E-4, E-5, E-6, E-7, E-8, E-9, E-10, E-11, E-12, E-13, E-14, E-15 or E-16 in Table 1, and the salts thereof.

A more preferred embodiment of the compounds of formula I according to this invention refers to compounds of formula I*****

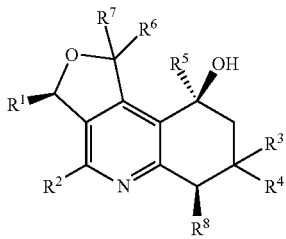
(I*****)

wherein the variables R¹-R⁸ are defined as hereinbefore and hereinafter, their tautomers, their stereoisomers, mixtures thereof, and the salts thereof.

This embodiment also includes compounds of formula I*****, wherein the variables R¹-R⁸ are selected from above definitions a) (a¹) to f) (f³), their tautomers, their stereoisomers, mixtures thereof, and the salts thereof.

Particularly, this embodiment refers to compounds of formula I***** as defined by the embodiment E-1, E-2, E-3, E-4, E-5, E-6, E-7, E-8, E-9, E-10, E-11, E-12, E-13, E-14, E-15 or E-16 in Table 1, and the salts thereof.

The invention further includes all mixtures of the stereoisomers mentioned herein independent of the ratio, including the racemates.

In a particular embodiment, the present invention refers to those compounds according to this invention where R³ and R⁴ together and with inclusion of the carbon atom, to which they are attached, form a cyclopropane ring.

A particularly preferred compound according to the invention is a compound selected from the group consisting of:

(3R,9S)-4-isopropyl-7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]-9-ol

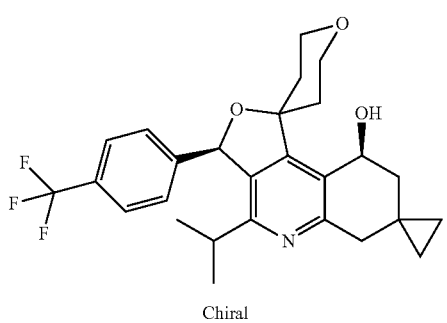 [SMILES: CC(C)c1nc2c(c3c1[C@@H](c1ccc(C(F)(F)F)cc1)OC31CCOCC1)[C@@H](O)CC1(CC1)C2]

5-((3R,9S)-9-hydroxy-4-isopropyl-7,7-(ethan-1,2-diyl)-2',3',5',6,6',7,8,9-octahydro-3H-spiro[furo[3,4-c]quinoline-1,4'-pyran]-3-yl)-2-(trifluoromethyl)benzonitrile

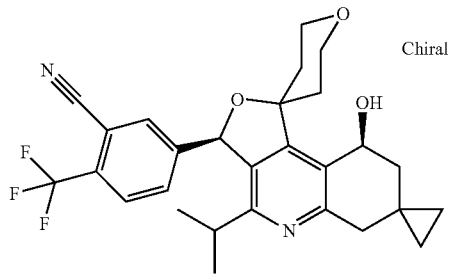 [SMILES: CC(C)c1nc2c(c3c1[C@@H](c1ccc(C(F)(F)F)c(C#N)c1)OC31CCOCC1)[C@@H](O)CC1(CC1)C2]

(3R,9S)-4-isopropyl-7,7-(ethan-1,2-diyl)-3-(3-methoxy-4-(trifluoromethyl)phenyl)-2',3',5',6,6',7,8,9-octahydro-3H-spiro[furo[3,4-c]quinoline-1,4'-pyran]-9-ol

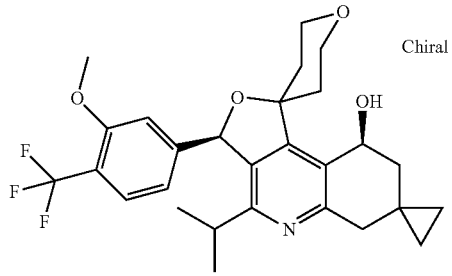 [SMILES: COc1cc([C@H]2OC3(CCOCC3)c3c2c(C(C)C)nc2c3[C@@H](O)CC3(CC3)C2)ccc1C(F)(F)F]

(3R,9S)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]-9-ol

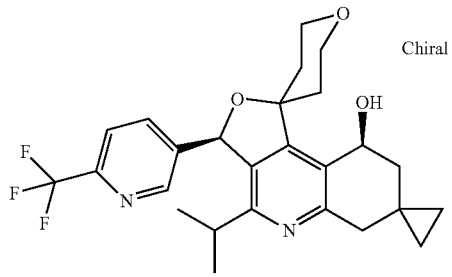 [SMILES: CC(C)c1nc2c(c3c1[C@@H](c1ccc(C(F)(F)F)nc1)OC31CCOCC1)[C@@H](O)CC1(CC1)C2]

(3R,6R,9S)-4-isopropyl-7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]-6,9-diol

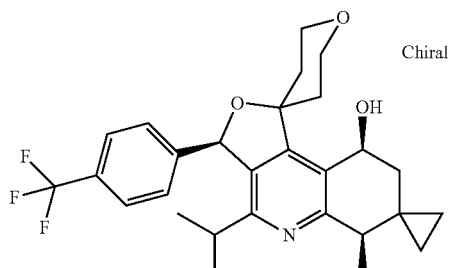

5-((3R,6R,9S)-6,9-dihydroxy-4-isopropyl-7,7-(ethan-1,2-diyl)-2',3',5',6,6',7,8,9-octahydro-3H-spiro[furo[3,4-c]quinoline-1,4'-pyran]-3-yl)-2-(trifluoromethyl)benzonitrile

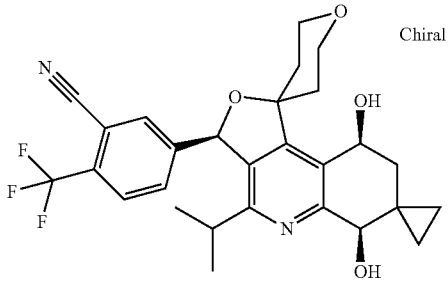 [SMILES: CC(C)c1nc2c(c3c1[C@@H](c1ccc(C(F)(F)F)c(C#N)c1)OC31CCOCC1)[C@@H](O)CC1(CC1)[C@H]2O]

(3R,6R,9S)-4-isopropyl-7,7-(ethan-1,2-diyl)-3-(3-methoxy-4-(trifluoromethyl)phenyl)-2',3',5',6,6',7,8,9-octahydro-3H-spiro[furo[3,4-c]quinoline-1,4'-pyran]-6,9-diol

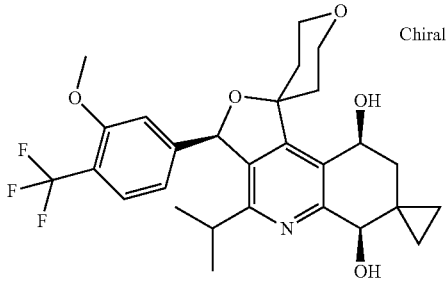 [SMILES: COc1cc([C@H]2OC3(CCOCC3)c3c2c(C(C)C)nc2c3[C@@H](O)CC3(CC3)[C@H]2O)ccc1C(F)(F)F]

and
(3R,6R,9S)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]-6,9-diol

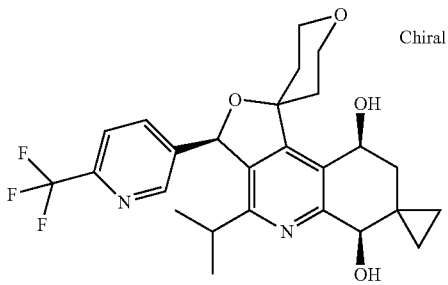 [SMILES: CC(C)c1nc2c(c3c1[C@@H](c1ccc(C(F)(F)F)nc1)OC31CCOCC1)[C@@H](O)CC1(CC1)[C@H]2O]

or a salt thereof.

Some terms used above and below in connection with the compounds according to the invention will now be defined more closely:

The term "substituted" as used herein means that any one or more hydrogens on the designated atom is replaced with a selection from the indicated group, provided that the designated atom's normal valence is not exceeded, and that the substitution results in a stable compound.

The term 1-nC-alkyl, alone or as part of another group, wherein n may have a value of 1 to 6, denotes a saturated, branched or unbranched aliphatic, acyclic hydrocarbon group having 1 to n C atoms. Examples of such groups may include, without being limited to, methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term 2-nC-alkenyl, alone or as part of another group, wherein n may have a value of 2 to 4, denotes an unsaturated, branched or unbranched aliphatic, acyclic hydrocarbon group having 2 to n C atoms and at least one C=C double bond. Examples of such groups may include, without being limited to, ethenyl, prop-1-en-1-yl, prop-1-en-2-yl, but-1-en-1-yl, but-1-en-2-yl, but-2-en-2-yl, etc.

The term halogen within the meaning of the present invention refers to fluorine, chlorine, bromine and iodine, of which fluorine, chlorine and bromine are more worthy to be mentioned.

The term 1-nC-alkoxy, alone or as part of another group, denotes a 1-nC-alkyl-O— group, wherein 1-nC-alkyl is as hereinbefore defined. Examples of such groups may include, without being limited to, methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy, etc.

The term 1-nC-alkoxy-1-nC-alkyl means a 1-nC-alkyl group as defined herein which is substituted by a 1-nC-alkoxy group as defined herein.

The term cyano-1-nC-alkyl means a 1-nC-alkyl group as defined herein which is substituted by a cyano group.

The term hydroxy-1-nC-alkyl means a 1-nC-alkyl group as defined herein which is substituted by a hydroxy group.

A mono- or bicyclic 5- to 10-membered aryl or heteroaryl group, which heteroaryl contains 1 to 4 heteroatoms selected from the group consisting of N, O and S, refers to a mono- or fused bicyclic 5- to 10-membered (fully or partially) aromatic or heteroaromatic ring system optionally comprising 0 to 4 heteroatoms selected from the group consisting of N, O and S.

An aryl group as mentioned herein, alone or as part of another group, refers to a carbocyclic, mono- or fused bicyclic (fully or partially) aromatic ring system having the indicated numbers of ring members. Representative 6- or 10-membered mono- or fused bicyclic aryl groups include, without being limited to, phenyl and naphthyl.

A heteroaryl group as mentioned herein, alone or as part of another group, refers to a heterocyclic, mono- or fused bicyclic (fully or partially) heteroaromatic ring system having the indicated numbers of ring members and containing 1 to 4 heteroatoms selected from nitrogen, oxygen and sulphur.

Representative 5-membered monocyclic heteroaryl groups include, without being limited to, thiophenyl (thienyl), furanyl, pyrrolyl, imidazolyl, pyrazolyl, thiazolyl, isothiazolyl, oxazolyl, isoxazolyl, thiadiazolyl, and oxadiazolyl, Representative 6-membered monocyclic heteroaryl groups include, without being limited to, pyridyl, pyrimidinyl, pyridazinyl, and pyrazinyl.

Representative 9-membered fused bicyclic groups include, without being limited to, indolyl, benzothiophenyl, benzofuranyl, benzimidazolyl, benzpyrazolyl (indazolyl), benzthiazolyl, benzoxazolyl, benzisothiazolyl, and benzisooxazolyl.

Representative 10-membered fused bicyclic heteroaryl groups include, without being limited to, quinolyl, isoquinolyl, and quinazolyl.

Among the 5- to 10-membered aryl or heteroaryl groups mentioned herein, thiophenyl, thiazolyl, phenyl, pyridyl, pyrimidinyl, pyridazinyl, pyrazinyl and naphthyl are more worthy to be mentioned.

The term 3-nC-cycloalkyl, alone or as part of another group, wherein n may have a value of 4 to 7, denotes a saturated, monocyclic, aliphatic hydrocarbon ring group having 3 to n ring C atoms. Examples of such groups may include, without being limited to, cyclopropyl, cyclobutyl, cyclopentyl, cyclohexyl and cycloheptyl, of which cyclopropyl, cyclobutyl, cyclopentyl and cyclohexyl are more worthy to be mentioned.

The term 3-nC-cycloalkane, alone or as part of another group, wherein n may have a value of 4 to 7, denotes a saturated, monocyclic, aliphatic hydrocarbon ring having 3 to n ring C atoms. Examples of such rings may include, without being limited to, a cyclopropane, cyclobutane, cyclopentane, cyclohexane and cycloheptane ring, of which cyclopropane, cyclobutane, cyclopentane and cyclohexane are more worthy to be mentioned.

The term 1-nC-alkyl-3-nC-cycloalkyl means a 3-nC-cycloalkyl group as defined herein which is substituted by a 1-nC-alkyl group as defined herein.

The term cyano-3-nC-cycloalkyl means a 3-nC-cycloalkyl group as defined herein which is substituted by a cyano group.

Completely or partially fluorine-substituted 1-nC-alkyl is, for example difluoromethyl, trifluoromethyl, pentafluoroethyl, 2,2-difluoroethyl, 2,2,2-trifluoroethyl, 1,1-difluoro-1-ethyl or 1,1,1,3,3,3-hexafluorisopropyl, of which trifluoromethyl is to be emphasized. In an embodiment, partially fluorine-substituted 1-nC-alkyl stands for predominantly fluorine-substituted 1-nC-alkyl. "Predominantly" in this connection means that more than half of the hydrogen atoms of the 1-nC-alkyl groups are replaced by fluorine atoms.

Completely or partially fluorine-substituted 1-nC-alkoxy is, for example difluoromethoxy, trifluoromethoxy, pentafluoroethoxy, 2,2-difluoroethoxy, 2,2,2-trifluoroethoxy or 1,1,1,3,3,3-hexafluorisopropoxy. In an embodiment, partially fluorine-substituted 1-nC-alkoxy stands for predominantly fluorine-substituted 1-nC-alkoxy. "Predominantly" in this connection means that more than half of the hydrogen atoms of the 1-nC-alkoxy groups are replaced by fluorine atoms.

In general, unless otherwise mentioned, heterocyclic groups mentioned herein include all the possible isomeric forms thereof, e.g. tautomers and/or positional isomers thereof. Thus, for example, the term pyridyl includes pyridine-2-yl, pyridine-3-yl and pyridine-4-yl.

Constituents which are substituted as stated herein, may be substituted, unless otherwise noted, at any possible position.

Further, unless otherwise noted, carbocyclic groups which are substituted as mentioned herein may be substituted by their given substituents or parent molecular groups at any possible position.

Further, the heterocyclic groups mentioned herein may be substituted by their given substituents or parent molecular groups, unless otherwise noted, at any possible position, such as e.g. at any substitutable ring carbon or ring nitrogen atom.

Further, unless otherwise noted, rings containing quaternizable amino- or imino-type ring nitrogen atoms (—N═) may be preferably not quaternized on these amino- or imino-type ring nitrogen atoms.

If residues, substituents or groups occur several times in a compound they may have the same or different meanings.

In general, for groups comprising two or more subgroups, the last named subgroup is the radical attachment point, for example, the substituent "1-nC-alkoxy-1-nC-alkyl" means a 1-nC-alkoxy group which is bound to a 1-nC-alkyl group, the latter of which is bound to the core or to the group to which the substituent is attached.

All atoms/elements, including atoms that are part of a group, described herein comprise all stable isotopic forms of the respective element. For instance, whenever hydrogen is mentioned, either explicitly or as part of a group such as methyl, this includes hydrogen and deuterium as stable isotopic forms of the element hydrogen.

Unless otherwise stated, the groups, residues and substituents, particularly $R^1$ to $R^8$, $R^7$, PG, $R^a$, $R^b$, $R^9$ to $R^{11}$ are defined as above and below.

If not otherwise specified, the substituents $R^9$, $R^{10}$ and/or $R^{11}$ can be attached in the ortho, meta or para position with respect to the binding position in which the aryl ring is bonded to the scaffold ring system, whereby emphasis is given to the attachment in the meta or in the para position.

Salts of the compounds of formula I according to the present invention include—depending upon their nature—all acid addition salts and all salts with bases, especially all pharmaceutically acceptable acid addition salts and salts with bases. Particular mention may be made of the physiologically tolerable salts with inorganic or organic acids or bases customarily used in pharmacy. The salts include water-insoluble and, particularly, water-soluble salts.

Inorganic acids suitable for forming pharmaceutically or physiologically acceptable acid addition salts include, by way of example and not limitation, hydrochloric acid, hydrobromic acid, phosphoric acid, sulfuric acid, and the like. Organic acids suitable for forming pharmaceutically or physiologically acceptable acid addition salts include, by way of example and not limitation, citric acid, maleic acid, fumaric acid, succinic acid, lactic acid, tartaric acid, methanesulfonic acid, and the like.

Thus, pharmaceutically or physiologically acceptable acid addition salts with inorganic or organic acids include, by way of example and not limitation, hydrochlorides, hydrobromides, phosphates, sulfates, citrates, maleates, fumarates, succinates, lactates, tartrates, methanesulfonates (mesylates), and the like.

Salts which are unsuitable for pharmaceutical uses but which can be employed, for example, for the isolation or purification of free compounds of formula I or their pharmaceutically acceptable salts, are also included.

Pharmaceutically non-acceptable salts, which can be obtained, for example, as process products during the preparation of the compounds according to this invention e.g. on an industrial scale, are converted into pharmaceutically acceptable salts by processes known to the person skilled in the art.

All isomeric forms (especially all regio- and stereoisomeric forms, e.g. all chiral, enantiomeric, diastereomeric, racemic forms, tautomeric and all geometric isomeric forms) of a compound of formula I are intended within this invention, unless the specific isomer form is specifically indicated. Obviously, the isomer which is pharmacologically most effective and most free from side effects is preferred.

It will be appreciated that the compounds of the present invention contain at least two asymmetrically substituted carbon atoms, and may be isolated as pure diastereomers or diastereomeric mixtures in optically active or racemic forms.

The compounds of formula I are chiral compounds having chiral centers at least in positions 3 and 9, as well as, depending on the meanings of $R^3$ and $R^4$, in position 7, depending on the meanings of $R^8$, in position 6 and, depending on the meanings of $R^6$ and $R^7$, in position 1.

Numbering:

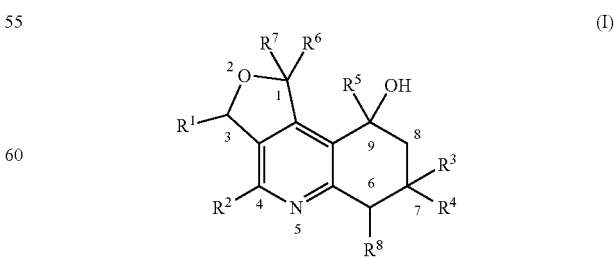

The invention contemplates all conceivable stereoisomers, particularly the diastereomers and enantiomers mentioned herein, e.g. in substantially pure form, in enriched form (e.g. substantially free of any or all other undesired diastereomers and/or enantiomers) and/or in any mixing ratio, including the racemic forms, as well as the salts thereof.

In general, substantially pure stereoisomers can be obtained according to synthetic principles customary to the skilled person, e.g. by separation of corresponding mixtures, by using stereochemically pure starting materials and/or by stereoselective synthesis.

It is known in the art how to prepare optically active forms, such as by resolution of racemic forms or by synthesis, e.g. from optically active starting materials and/or by using chiral reagents.

Enantiomerically pure compounds of this invention can be prepared via asymmetric synthesis, for example by preparation and separation of appropriate diastereoisomeric compounds/intermediates which can be separated by known methods (e.g. by chromatographic separation or (fractional) crystallization from a suitable solvent), and/or by using chiral reaction components (e.g. chiral reagents, chiral catalysts, chiral ligands, chiral synthons, chiral building blocks, or the like).

Further, it is known to the person skilled in the art how to prepare enantiomerically pure compounds from the corresponding racemic mixtures, such as e.g. by chromatographic separation of the corresponding racemic compounds on chiral separating columns; or by resolution of racemic compounds using an appropriate resolving agent; e.g. by means of diastereomeric salt formation of the racemic compounds with optically active acids or bases, subsequent resolution of the salts and release of the desired compound from the salt; or by derivatization of the corresponding racemic compounds with chiral auxiliary reagents, subsequent diastereomer separation and removal of the chiral auxiliary group; by kinetic resolution of a racemate (e.g. by enzymatic resolution); by enantioselective (preferential) crystallization (or crystallization by entrainment) from a conglomerate of enantiomorphous crystals under suitable conditions; or by (fractional) crystallization from a suitable solvent in the presence of a chiral auxiliary.

Biological Assay

The biological properties of the new compounds may be investigated as follows:

CETP In Vitro Assay

CETP inhibitory activity of compounds of the present invention can be determined in a fluorometric assay purchased from Roar Biomedical, Inc. (New York, N.Y., USA). The compounds of the present invention inhibit CETP-dependent cholesterol ester transfer from HDL to LDL as described here. Recombinant human CETP was partially purified from medium conditioned by CETP expressing CHO cells. In a 384 well format 2.5 µl of compound solution in DMSO was combined with 2 µl of donor solution, 2 µl of acceptor solution and 0.8 µl of recombinant human CETP solution in a total volume of 100 µl with assay buffer and incubated for 3 hours at 37° C. The fluorescence intensity was measured at excitation wavelength of 485 nm and emission wavelength of 535 nm. $IC_{50}$ values are calculated from dose effect curves from compound concentrations between 1 nM and 30 µM.

The compounds of general formula I according to the invention for example have $IC_{50}$ values below 10000 nM, preferably below 2000 nM, more preferably below 400 nM, even more preferably below 100 nM and most preferably below 50 nM or below 20 nM. The $IC_{50}$ values of the examples compiled in the experimental part are provided in the following Table 2.

TABLE 2

$IC_{50}$ values for inhibition of CETP by the examples compiled in the experimental part

| Example | $IC_{50}$ [nM] |
|---------|----------------|
| 1 | 15 |
| 2 | 18 |
| 3 | 11 |
| 4 | 90 |
| 5 | 9 |
| 6 | 43 |
| 7 | 11 |
| 8 | 210 |

Assay for Metabolic Degradation

The metabolic degradation of the test compound is assayed at 37° C. with pooled human liver microsomes. The final incubation volume of 100 µl per time point contains TRIS buffer pH 7.6 at room temperature (0.1 M), magnesium chloride (5 mM), microsomal protein (1 mg/ml) and the test compound at a final concentration of 1 µM.

Following a short preincubation period at 37° C., the reactions were initiated by addition of beta-nicotinamide adenine dinucleotide phosphate, reduced form (NADPH, 1 mM) and terminated by transferring an aliquot into solvent after different time points. Additionally, the NADPH-independent degradation was monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t ½) is determined by the slope of the semilogarithmic plot of the concentration-time profile.

For example, the compounds of general formula I according to the invention typically have metabolic half-life times in human liver microsomes of above 50 min, preferably above 100 min, more preferably above 130 min.

TABLE 3 half-life (t½) values for human liver microsomal metabolic degradation for representative examples compiled in the experimental part

| Example | t½ [min] |
|---------|----------|
| 1 | >130 |
| 2 | >130 |
| 5 | 57 |
| 8 | >130 |

Accordingly, the compounds of the present invention have good inhibitory activity on CETP and have prolonged metabolic stability, particularly in human liver microsomes.

Indications

The compounds of formula I and their physiologically tolerable salts according to the present invention have valuable pharmacological properties which make them commercially applicable. Thus, for example, these compounds can act as inhibitors of CETP and are expected to be commercially applicable in the therapy of diseases responsive to the inhibition of CETP, such as e.g. any of those diseases mentioned herein.

In view of their ability to inhibit cholesterol ester transfer protein (CETP), the compounds of general formula I according to the invention and the corresponding pharmaceutically acceptable salts thereof are theoretically suitable for the treatment and/or prevention of all those conditions or diseases which may be affected by the inhibition of the cholesterol ester transfer protein (CETP) activity. Therefore, compounds according to the invention are particularly suitable for the treatment and/or prevention of cardiovascular and/or cardiometabolic and related disorders, in particular atherosclerosis, peripheral vascular disease, dyslipidemia (including e.g. mixed dyslipidemia), hyperbeta-lipoproteinemia, hypoalpha-lipoproteinemia, hypercholesterolemia, hypertriglyceridemia, hyperlipidemia, hypolipoproteinemia, hyperlipoproteinemia, hypo-HDL cholesterolemia, hyper-LDL cholesterolemia, familial hypercholesterolemia, angina, ischemia, cardiac ischemia, stroke, myocardial infarction, reperfusion injury, angioplastic restenosis, hypertension, endothelial dysfunction, vascular complications of diabetes, prevention of diabetes, insulin resistance, obesity, metabolic syndrome, diabetes (especially type 2 diabetes meliitus) or endotoxemia, or arteriosclerosis, coronary heart disease, coronary artery disease, coronary vascular disease or congestive heart failure.

Application Forms and Dosages

The compounds of formula I and their pharmaceutically acceptable salts can be used as medicaments, e.g. in the form of pharmaceutical compositions for enteral, parenteral or topical administration. They may be administered in any of the generally accepted modes of administration available in the art, e.g., perorally, e.g. in the form of tablets, coated tablets, dragees, hard and soft gelatine capsules, solutions, emulsions or suspensions, rectally, e.g. in the form of suppositories, parenterally (including intravenously), e.g. in the form of injection solutions or infusion solutions, or topically, e.g. in the form of ointments, creams or oils. Among the possible modes of administration, oral and intravenous delivery are preferred.

The pharmaceutical compositions according to this invention contain at least one of the compounds of the invention (=active compound), e.g. in a total amount of from 0.1 to 99.9 wt %, 5 to 95 wt %, or 20 to 80 wt %, optionally together with pharmaceutically acceptable excipients.

The person skilled in the art is familiar with pharmaceutically acceptable excipients, such as e.g. diluents, carriers, binders, disintegrants, surfactants, lubricants, vehicles, auxiliaries, adjuvants and/or further additives which are known to be suitable for preparing pharmaceutical compositions, on account of his/her expert knowledge.

As pharmaceutically acceptable excipients, usually any excipients known to be appropriate for pharmaceutical compositions come into consideration. Examples thereof include, but are not limited to, diluents, fillers, binders, disintegrants, lubricants, glidants, solvents, dispersants, emulsifiers, solubilizers, gel formers, ointment bases, antioxidants, preservatives, stabilizers, carriers, thickeners, complexing agents, buffers, pH regulators (e.g. to obtain neutral, alkaline or acidic formulations), permeation promoters, polymers, coating agents, propellants, tonicity adjusting agents, surfactants, colorants, flavorings, sweeteners and dyes.

In general, suitable carrier materials are not only inorganic carrier materials, but also organic carrier materials. Thus, e.g., lactose, starches (e.g. corn starch) or derivatives thereof, talc, silica, polyvinylpyrrolidones, stearic acid or its salts can be used as carrier materials for tablets, coated tablets, dragees and hard gelatine capsules. Suitable carrier materials for soft gelatine capsules are, e.g., vegetable oils, waxes, fats and semi-solid and liquid polyols. Suitable carrier materials for the production of solutions and syrups are, e.g., water, polyols, sucrose, invert sugar and the like. Suitable carrier materials for injection or infusion solutions are, e.g., water, alcohols, polyols, glycerol and vegetable oils. Suitable carrier materials for suppositories are, e.g., natural or hardened oils, waxes, fats and semi-liquid or liquid polyols or polyethylene glycols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

In particular, excipients, carriers and/or diluents of a type appropriate to the desired pharmaceutical composition, formulation or preparation and the desired mode of administration are used.

The pharmaceutical compositions according to this invention can be prepared by processes which are known per se and familiar to the person skilled in the art, e.g. by incorporating the described compounds of formula I or their pharmaceutically acceptable salts (optionally combined with other active substances) optionally together with one or more conventional carriers (e.g. solid or liquid carriers) and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions or suppositories.

The dosage of the compounds of the invention (=active compounds) can vary within wide limits depending on the compound which is to be administered, the nature and gravity of the disease to be treated or prevented, the age and the individual condition of the patient and the mode and frequency of administration, and will, of course, be fitted to the individual requirements in each particular case. Usually, a dosage of the compounds of the invention (=active compounds) in the order of magnitude customary for CETP inhibitors comes into consideration. Expediently, the dosage may be from 0.1 ng/ml to 10 mg/ml, preferably 1 ng/ml to 10 mg/ml, by intravenous route, and 0.1 to 2000 mg, preferably 1 to 100 mg, by oral route, in each case administered 1 to 4 times a day. Depending on the dosage it may be convenient to administer the daily dosage in several dosage units.

Combinations

Besides their use in monotherapy, the compounds according to the invention may also be used in conjunction with other active substances, particularly for the treatment and/or prevention of the diseases, disorders and conditions mentioned above.

Other active substances which are suitable for such a combination include for example those which potentiate the therapeutic effect of a cholesterol ester transfer protein (CETP) inhibitor according to the invention with respect to one of the indications mentioned and/or which allow the dosage of a cholesterol ester transfer protein (CETP) inhibitor according to the invention to be reduced.

Therapeutic agents which are suitable for such a combination include particularly one or more lipid modulating agents. Lipid modulating agents comprise HMG CoA reductase inhibitors (e.g. simvastatin, atorvastatin), fibrates (e.g. bezafibrate, fenofibrate), nicotinic acid and the derivatives thereof, PPAR ($\alpha$, $\gamma$ or $\alpha/\gamma$) agonists or modulators, ACAT inhibitors (e.g. avasimibe), MTP inhibitors, squalene cyclase and squalene synthase inhibitors, LXR agonists or modulators, bile acid-binding substances such (e.g. cholestyramine, colesevelam), cholesterol absorption inhibitors (e.g. ezetimibe), niacin, PCSK9 inhibitors, bile acid reuptake inhibitors and lipase inhibitors.

Other therapeutic agents which are suitable for such a combination include one or more antidiabetic agents as for example metformin, alpha-glucosidase inhibitors (e.g. acarbose, voglibose), PPAR ($\alpha$, $\gamma$ or $\alpha/\gamma$) agonists or modulators, DPP-IV inhibitors (e.g. Sitagliptin, Vildagliptin, Saxagliptin, Alogliptin, Linagliptin), SGLT 2 inhibitors (e.g. dapagliflozin, sergliflozin), GLP-1 or GLP-1 analogues (e.g. exenatide, liraglutide), insulin or insulin analogues, sulphonylureas (e.g. glibenclamide, tolbutamide, glimepiride), thiazolidinediones (e.g. rosiglitazone, pioglitazone), nateglinide, repaglinide, II-β-HSD inhibitors, glucose-6-phosphatase inhibitors, fructose-1,6-bisphosphatase inhibitors, glycogen phosphorylase inhibitors, glucagon receptor antagonists, inhibitors of phosphoenol pyruvate carboxykinase, glycogen synthase kinase or pyruvate dehydrokinase and glucokinase activators.

Also suitable for such a combination are one or more antiobesity agents including for example sibutramine, tetrahydrolipostatin, leptin, leptin mimetics, antagonists of the cannabinoid) receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure or chronic heart failure such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

The therapeutic agents mentioned herein above as combination partners of the compounds according to this invention are meant to include pharmaceutically acceptable derivatives thereof, such as e.g. their pharmaceutically acceptable salts. The person skilled in the art is aware on the base of his/her expert knowledge of the kind, total daily dosage(s) and administration form(s) of the additional therapeutic agent(s) coadministered. Said total daily dosage(s) can vary within a wide range. Usually, the dosage for the combination partners mentioned above is ⅕ of the lowest dose normally recommended up to 1/1 of the normally recommended dose.

In practicing the present invention, the compounds according to this invention may be administered in combination therapy separately, sequentially, simultaneously, concurrently or chronologically staggered with one or more further active substances, such as e.g. any of the therapeutic agents mentioned herein above as a combination partner.

In this context, the present invention further relates to a combination comprising a first active ingredient, which is at least one compound according to this invention, and a second active ingredient, which is at least one of the active substances described above as a combination partner, for separate, sequential, simultaneous, concurrent or chronologically staggered use in therapy, particularly for treatment and/or prevention of cardiovascular or related disorders, such as e.g. any of those mentioned herein.

Further, this invention relates to the use of a compound according to this invention combined with at least one of the active substances described above as a combination partner, for preparing a pharmaceutical composition which is suitable for the treatment or prevention of diseases or conditions which may be affected by the inhibition of the cholesterol ester transfer protein (CETP) activity, particularly cardiometabolic and/or cardiovascular disorders, more particularly one of the diseases, disorders or conditions listed above.

Further, this invention relates to a pharmaceutical composition which comprises a compound according to the invention and at least one of the active substances described above as combination partners, optionally together with one or more inert carriers and/or diluents.

The term "combination" according to this invention may be present as a fixed combination, a non-fixed combination, a free combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The first and second active ingredient of a kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount, particularly for the treatment and/or prevention of the diseases, disorders and conditions mentioned above.

General Synthesis

The compounds according to the invention may be obtained using methods of synthesis known in principle. Preferably the compounds are obtained by the following methods according to the invention which are described in more detail hereinafter.

The synthesis of compounds of formula I, wherein $R^1$-$R^7$ are defined as hereinbefore, $R^8$ denotes hydrogen, can be carried out according to the invention related process a) shown in scheme 1.

Scheme 1 (Process a)):

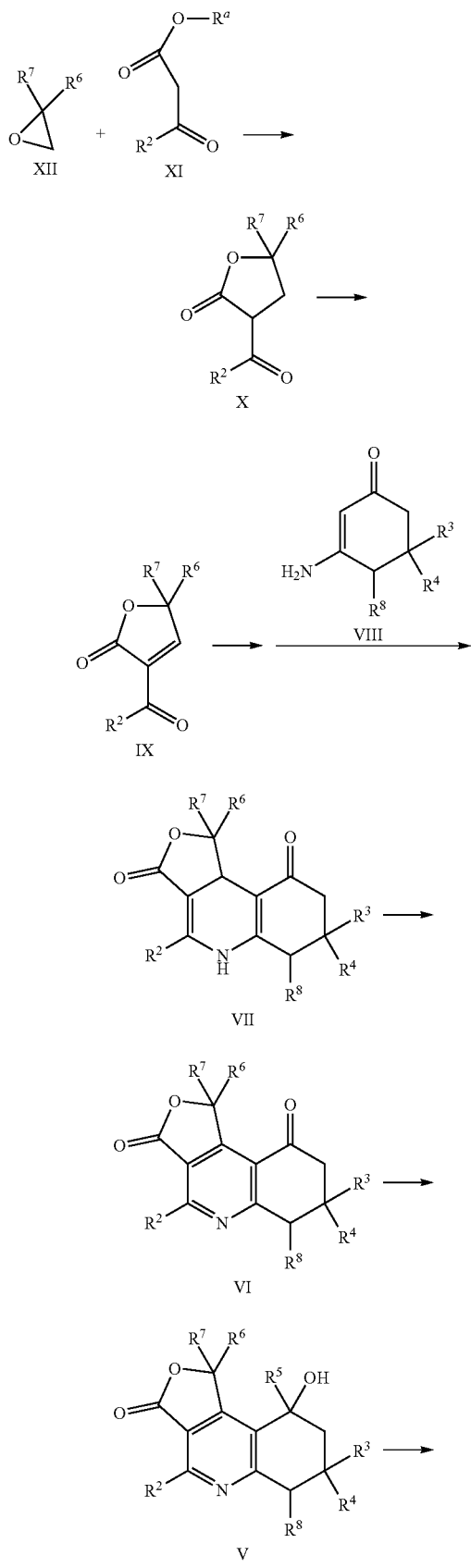

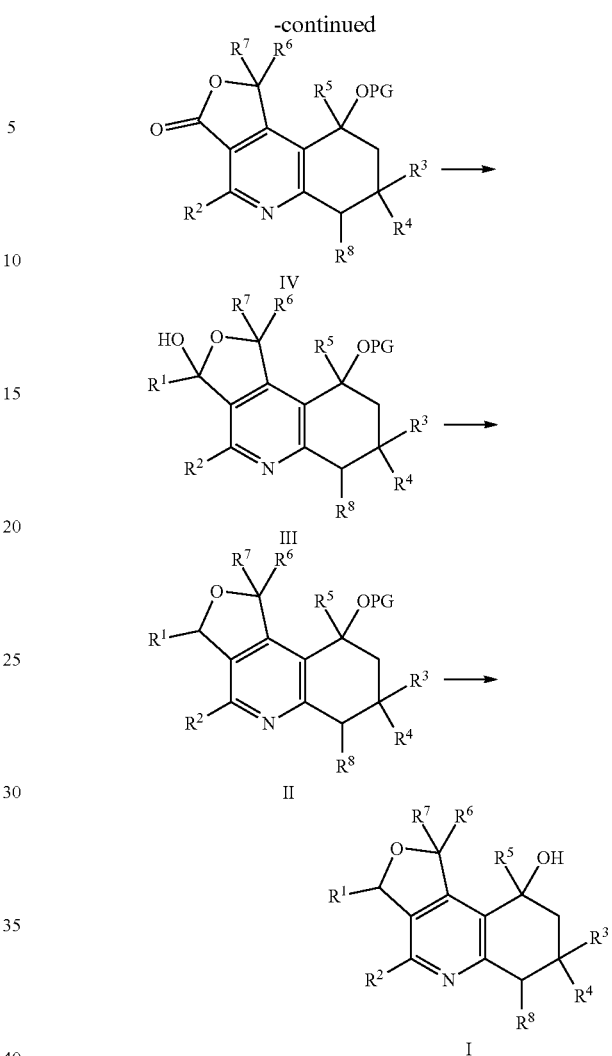

In the first step of this route ketoesters of formula XI, wherein $R^a$ denotes methyl or ethyl, in a suitable solvent such as e.g. methanol or ethanol are deprotonated with a suitable base such as e.g. sodium ethoxide or sodium methoxide and treated with epoxides of formula XII at temparatures between −10° C. and 80° C. to give ketolactones X.

Ketolactones X are oxidized to furanones IX with a suitable oxidizing reagent such as e.g. 2-iodoxybenzoic acid and 4-methoxypyridine-N-oxide in a suitable solvent such as e.g. dimethylsulfoxide at temperatures between 0° C. and 50° C.

Furanones of formula IX are condensed with enaminoketones of formula VIII, e.g. at temperatures between 150° C. and 250° C. either neat under reduced pressure at or at temperatures between 100° C. and 150° C. in a suitable solvent such as e.g. acetic acid yielding the tricyclic dihydropyridines of formula VII.

Dihydropyridines VII are oxidized to the corresponding tricyclic pyridines of formula VI using a suitable oxidizing reagent such as e.g. 2,3-dichloro-5,6-dicyano-1,4-benzoquinone (DDQ) in a suitable solvent such as e.g. dichloromethane at temperatures between 0° C. and 50° C. Reduction of the ketogroup in tricyclic pyridines of formula VI is carried out with a suitable hydride donating reagent such as e.g. borane-tetrahydrofurane-complex, borane-dimethylsulfide-complex, borane-dimethylaniline-complex, borane-diethylaniline-complex, sodium borohydride, lithium borohydride, lithium aluminium hydride in a suitable solvent such as e.g. diethylether, tetrahydrofurane, 1,4-dioxane or toluene, at temperatures between −78° C. and 100° C., but preferably between −50° C. and 80° C., optionally in the presence of a chiral ligand as for example (1R,2S)-(+)-cis-1-Amino-2-indanol, (1S,2R)-(−)-cis-1-Amino-2-indanol, (R)-1-Methyl-3,3-diphenyl-tetrahydro-pyrrolo[1,2-c][1,3,2]oxazaborole or (S)-1-Methyl-3,3-diphenyl-tetrahydro-pyrrolo[1,2-c][1,3,2]oxazaborole gives the alcohols of formula V, wherein $R^5$ denotes hydrogen. The reduction in the presence of chiral ligands results in enantiomerically enriched compounds of formula V. For example the reduction with borane reagents such as e.g. borane-tetrahydrofurane-complex, borane-dimethylsulfide-complex, borane-dimethylaniline-complex or borane-diethylaniline-complex each in the presence of (1R,2S)-(+)-cis-1-Amino-2-indanole gives compounds of formula V with S-configuration at the newly formed stereocenter as it is known from the literature (see *Tetrahedron: Asymmetry* 1995, 6, 301-306; *Synthesis* 1998, 937-961 or *Angew. Chem.* 1999, 111, 3574-3576). Likewise, alkylation reaction of compounds of formula V with a suitable alkyl metal compound, such as e.g. 1-4C-dialkylzinc-, 1-4C-alkylmagnesium halogenide-, or 1-4C-alkyllithium-reagent, particularly 1-2C-dialkylzinc-, 1-2C-alkylmagnesium halogenide-, or 1-2C-alkyllithium-reagent, in a suitable solvent such as e.g. n-hexane, cyclohexane, toluene, diethylether, tetrahydrofurane or 1,4-dioxane, optionally in the presence of a chiral ligand such as for example (R)-1-methyl-3,3-diphenyl-tetrahydro-pyrrolo[1,2-c][1,3,2]oxazaborole, (R)-1-methyl-3,3-diphenyl-tetrahydro-pyrrolo[1,2-c][1,3,2]oxazaborole, (−)-3-exo-dimethylamino-isoborneol, (+)-3-exo-dimethylamino-isoborneol or ligands as described in *J. Am. Chem. Soc.* 2002, 124, 10970-10971 or *Tetrahedron* 1998, 54, 5651-5666, at temperatures between −50° C. and 100° C., but preferably between −20° C. and 70° C., gives the corresponding compounds of formula V, wherein $R^5$ denotes 1-4C-alkyl, particularly 1-2C-alkyl.

The alcohol group in compounds of formula V can be temporarily protected with a suitable protecting group, e.g. as a tert.-butyldimethylsilylether by the reaction with tert.-butyldimethylsilylchloride in a solvent such as e.g. dimethylformamide or acetonitrile in the presence of imidazole, at temperatures between −20° C. and 120° C., but preferably between 0° C. and 80° C., to give the protected derivatives of formula IV, in which PG stands for this suitable protecting group. This protection can also be carried out by reacting compounds of formula V with tert.-butyldimethylsilyl-trifluormethansulfonat in the presence of a base such as e.g. pyridine or 2,6-lutidine in a solvent such as e.g. dichloromethane, diethylether, tetrahydrofurane, 1,4-dioxane or toluene, at temperatures between −50° C. and 100° C. but preferably between −30° C. and 50° C. Alternatively any other suitable protecting group as described e.g. in "*Protective Groups in Organic Synthesis*", $2^{nd}$ edition, Greene T. W., Wuts P. G. M.; Wiley-Interscience: New York, 1991 or in "*Protective Groups*", Kocienski P. J.; Thieme: New York, 1994 can be used.

Lactones of formula IV are transformed into lactols of formula III by reaction with a suitable $R^1$-metal reagent, such as e.g. $R^1$-magnesium halogenide- or $R^1$-lithium-reagent, in an aprotic solvent such as e.g. diethylether, tetrahydrofurane, 1,4-dioxane or toluene, at temperatures between −78° C. and room temperature for lithium reagents or between −50° C. and room temperature for magnesium reagents.

The lactols of formula III are reduced to the corresponding compounds of formula II using a combination of a suitable acid such as e.g. titaniumtetrachloride or borontrifluoride etherate with a suitable hydride donating reagent such as e.g. sodium borohydride, sodium cyanoborohydride or sodium triacetoxyborohydride, but preferably with sodium triacetoxyborohydride, in a suitable solvent such as e.g. diethylether, dichloromethane, toluene or tetrahydrofurane, but preferably tetrahydrofurane, at temperatures between −50° C. and room temperature. The reduction under preferred conditions results in diastereomerically enriched compounds of formula II. For example the reduction with borane reagents such as e.g. sodium triacetoxyborohydride in the presence of titaniumtetrachloride gives compounds of formula II, in which the newly formed stereocenter has preferably R-configuration as proven by extensive NMR analysis.

Deprotection of compounds of formula II, wherein PG denotes tert.-butyldimethylsilyl, preferably with a fluoride reagent such as e.g. tetrabutylammonium fluoride or caesium fluoride or with an acid such as e.g. for example trifluoroacetic acid, hydrochloric acid or sulphuric acid in a suitable solvent such as e.g. dichloromethane, 1,2-dichloroethane, diethylether, tetrahydrofurane, 1,4-dioxane, acetonitrile or toluene, at temperatures between −50° C. and 120° C., but preferably between −20° C. and 80° C. gives compounds of formula I. Alternatively any other protecting group introduced before can be cleaved by suitable methods as described in the literature e.g. in "*Protective Groups in Organic Synthesis*", $2^{nd}$ edition, Greene T. W., Wuts P. G. M.; Wiley-Interscience: New York, 1991 or in "*Protective Groups*", Kocienski P. J.; Thieme: New York, 1994.

Compounds of formula II can also be transformed into compounds of formula I, wherein $R^8$ denotes acetoxy, propionyloxy or hydroxy, according to invention related process b) shown in scheme 2.

The synthesis of compounds of formula I, wherein $R^1$-$R^7$ are defined as hereinbefore, $R^8$ denotes acetoxy, propionyloxy or hydroxy, can be carried out according to the invention related process b) shown in scheme 2, wherein PG denotes a suitable protecting group, starting from compounds of formula XIII, which equal compounds II in which $R^8$ denotes hydrogen.

Scheme 2 (Process b)):

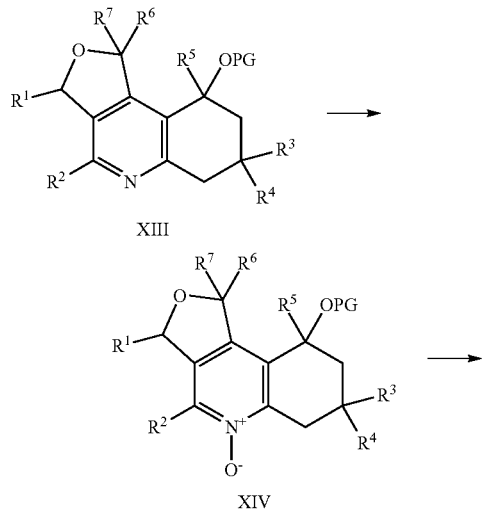

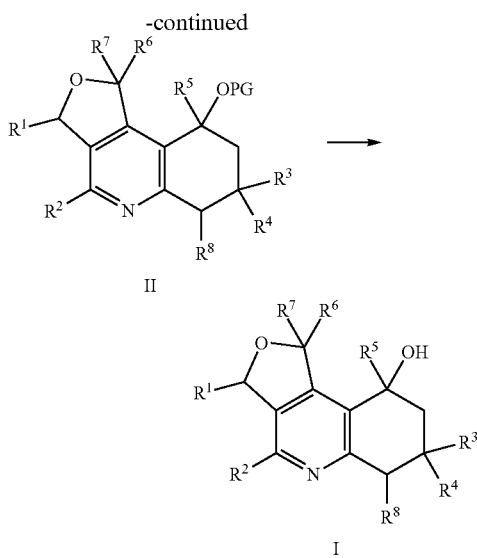

First step is the formation of N-oxides of formula XIV. This reaction is performed by treating compounds of formula XIII with a suitable oxidizing reagent, such as e.g. meta-chloroperbenzoic acid (MCPBA), in a suitable solvent such as e.g. dichloromethane, 1,2-dichloroethane, chloroform or tetrachloromethane, at temperatures between −10° C. and 60° C. Compounds of formula XIV are then reacted with acetic acid anhydride or propionic acid anhydride at temperatures between 90° C. and 180° C. to deliver compounds of formula II, wherein $R^8$ denotes acetoxy or propionyloxy. Deprotection of compounds of formula II, wherein PG denotes tert.-butyldimethylsilyl, preferably with a fluoride reagent such as e.g. tetrabutylammonium fluoride or caesium fluoride or with an acid such as e.g. trifluoroacetic acid, hydrochloric acid or sulphuric acid in a suitable solvent such as e.g. dichloromethane, 1,2-dichloroethane, diethylether, tetrahydrofurane, 1,4-dioxane, acetonitrile or toluene, or methanol or water, or mixtures thereof, at temperatures between −50° C. and 120° C., but preferably between −20° C. and 80° C., gives compounds of formula I, wherein $R^8$ denotes acetoxy or propionyloxy. Alternatively any other protecting group introduced before can be cleaved by suitable methods as described in the literature e.g. in "Protective Groups in Organic Synthesis", $2^{nd}$ edition, Greene T. W., Wuts P. G. M.; Wiley-Interscience: New York, 1991 or in "Protective Groups", Kocienski P. J.; Thieme: New York, 1994. Treating compounds of formula I, wherein $R^8$ denotes acetoxy or propionyloxy, with a suitable base such as e.g. sodium carbonate, potassium carbonate, caesium carbonate, lithium hydroxide, sodium hydroxide or potassium hydroxide in a suitable solvent such as e.g. methanol, ethanol, tetrahydrofurane, water or in a mixture of water and methanol or ethanol, at temperatures between 0° C. and 80° C., delivers compounds of formula I, wherein $R^8$ denotes hydroxy. Alternatively these compounds of formula II, wherein the −OPG group and the $R^8$ residue are cis configured, can be treated with a suitable base such as e.g. sodium carbonate, potassium carbonate, caesium carbonate, lithium hydroxide, sodium hydroxide or potassium hydroxide in a suitable solvent like methanol, ethanol or water or in a mixture of water and methanol or ethanol, at temperatures between 0° C. and 80° C., to deliver directly compounds of formula I, wherein $R^8$ denotes hydroxy.

Starting compounds of formulae VIII, XI, XII are known or can be obtained analogously or similarly to known procedures. Compounds of formula VIII can for example be prepared from their corresponding cyclohexan-1,3-diones analogous as described in Synthesis 1983, 902-903. The cyclohexandiones can be prepared analogous to the described procedure in Angew. Chem. 1999, 111, 3574-3576.

Besides the strategies presented a host of additional approaches can be envisaged. Therefore, the preceding strategies are in no way meant to restrict the possible synthetic pathways to access the compounds of the invention but are only supposed to show a few routes by way of example.

Besides the hereinbefore described methods for the synthesis of compounds of formula I, additional functional group transformations, which are known to the person skilled in the art, at any stage of the synthesis can be envisaged, if these transformations are compatible to other functional groups and if the so installed functional groups are stable to subsequent transformations in the synthesis.

For example aromatic hydroxy groups can be converted into aromatic sulfonyloxy groups such as methylsulfonyloxy, tosylsulfonyloxy or trifluoromethylsulfonyloxy. This transformation is performed by reacting compounds with aromatic hydroxy group with a sulfonyl anhydride, sulfonylchloride or sulfonylimide in a solvent such as e.g. dichloromethane, 1,2-dichloroethane, diethylether, tetrahydrofurane, 1,4-dioxane, acetonitrile or toluene at temperatures between −78° C. and 40° C., in the presence of a base such as e.g. triethylamine, N,N-diisopropyl-N-ethyl-amine, pyridine or 2,6-lutidine, optionally in the presence of an acylation catalyst as 4-dimethylamino-pyridine (DMAP).

These aromatic sulfonyloxy groups can be further transformed into alkenyl groups or optionally substituted cyclopropyl groups by reacting the compounds with aromatic sulfonyloxy groups with potassium alkenyltrifluoroborates, alkenyl-boronic acids, alkenyl-boronic acid pinacol esters, optionally substituted cyclopropyl-boronic acids or optionally substituted cyclopropyl-boronic acid pinacol esters in toluene, N,N-dimethylformamide, isopropanol, acetonitrile, 1,4-dioxane or tetrahydrofurane or mixtures of toluene and tetrahydrofurane in the presence of a base as such as e.g. aqueous sodium carbonate, aqueous potassium carbonate, aqueous caesium carbonate, silver carbonate, caesium fluoride, triethylamine or N,N-diisopropyl-N-ethyl-amine and in the presence of a catalyst such as e.g. tetrakis-triphenylphosphine-palladium-(0), bis-tri-tert.-butylphosphine-palladium-(0), 1,1'-bis-(diphenylphosphino)-ferrocene-dichloro-palladium-(II) or bis-[1,2-bis-(diphenylphosphino)-ethane]-palladium-(0), or in the presence of a palladium source such as e.g. palladium diacetate or tris-(dibenzylideneacetone)-dipalladium-(0) and a suitable ligand like e.g. tri-tert.-butylphosphine, tri-cyclohexylphosphine, di-adamantan-1-yl-butylphosphine, 2-dicyclohexylphosphino-2',6'-diisopropoxy-1,1'biphenyl, 2-dicyclohexylphosphino-2',4',6'-triisopropyl-1,1'-biphenyl or 2-dicyclohexylphosphino-2',6'-dimethoxy-1,1'-biphenyl at temperatures between 0° C. and 180° C., but preferably between room temperature and 120° C. Alkenyl groups can be transformed into an optionally substituted cyclopropyl group by a Simmons-Smith reaction. This reaction is performed by reacting with bromo-iodomethane or diiodomethane and diethylzinc, optionally in the presence of trifluoroacetic acid, in a solvent such as e.g. dichloromethane, 1,2-dichloroethane, diethylether, tetrahydrofurane, 1,4-dioxane or toluene at temperatures between −50° C. and 80° C., but preferably between −10° C. and room temperature.

Alkoxycarbonyl groups can be transformed into dialkylmethanol groups. This transformation is performed by reacting with an alkyllithium reagent or with an alkyl-Grignard reagent in a solvent such as e.g. diethylether, tetrahydrofurane, 1,4-dioxane or toluene at temperatures between −50° C. and 80° C., but preferably between −20° C. and room temperature. Alternatively alkoxycarbonyl groups, can be transformed into compounds hydroxymethyl groups. This transformation is performed by reacting with a reducing reagent such as e.g. lithiumaluminium hydride in a solvent like diethylether, tetrahydrofurane, 1,4-dioxane or toluene at temperatures between −50° C. and 80° C., but preferably between −20° C. and 40° C.

Hydroxy groups can be further transformed into alkoxy groups by alkylation. This transformation is performed by reacting with an alkylating agent such as e.g. an alkyl halogenide, methanesulfonic acid-alkyl-ester, p-toluenesulfonic acid-alkyl-ester or trifluoromethanesulfonic acid-alkyl-ester in the presence of a base such as e.g. sodium hydride, potassium hydride, sodium hexamethyldisilazide or potassium hexamethyldisilazide in a solvent such as e.g. diethylether, tetrahydrofurane, 1,4-dioxane, N,N-dimethylformamide, acetonitrile or toluene at temperatures between −50° C. and 80° C., but preferably between −20° C. and 50° C.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3rd Ed.) or in "Protecting Groups (Thieme Foundations Organic Chemistry Series N Group" by P. Kocienski (Thieme Medical Publishers, 2000).

In the reactions described hereinbefore, any reactive groups present such as carboxy-, carbonyl-, hydroxy-, amino-, alkylamino- or imino-groups may be protected during the reaction by conventional protecting groups which are cleaved again after the reaction.

For example, a protecting group for a carboxy group may be the methyl-, ethyl-, tert.-butyl- or benzyl-group.

For example, a protecting group for a carbonyl group may be an acetal or ketal like the 1,3-dioxolane- or the 1,3-dioxane-group.

For example, a protecting group for a hydroxy group may be a trimethylsilyl-, tert.-butyldimethylsilyl-, acetyl-, trityl-, benzyl- or tetrahydropyranyl-group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

The cleavage of a carboxymethyl- or a carboxyethyl-group can for example be carried out hydrolytically in an aqueous solvent, e.g. in water, methanol/water, isopropanol/water, acetic acid/water, tetrahydrofuran/water or 1,4-dioxane/water, in the presence of an acid such as trifluoroacetic acid, hydrochloric acid or sulphuric acid or in the presence of an alkali base as for example lithium hydroxide, sodium hydroxide or potassium hydroxide, but preferably sodium hydroxide, or aprotically in the presence of e.g. iodotrimethylsilane, at temperatures between 0 and 120° C., preferably at temperatures between 10 and 100° C.

An acetal or ketal can be cleaved with acetic acid, trifluoroacetic acid, hydrochloric acid, sulphuric acid or pyridiumium-p-toluene sulfonate in mixtures with water or in organic solvents like for example dichloromethane, 1,2-dichloroethane, tetrahydrofurane, 1,4-dioxane, toluene or acetone at temperatures between −20° C. and 150° C., but preferably between 0° C. and 120° C.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetatetetrahydrofurane, 1,4-dioxane or glacial acetic acid, optionally with the addition of an acid such as hydrochloric acid or with the addition of a base such as triethylamine at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as dichloromethane, 1,4-dioxane, methanol or diethylether.

A trimethylsilyl- or tert.-butyldimethylsilyl-group is cleaved with a fluoride reagent like for example tetrabutylammonium fluoride or caesium fluoride or with an acid like for example trifluoroacetic acid, hydrochloric acid or sulphuric acid in a solvent like e.g. dichloromethane, 1,2-dichloroethane, diethylether, tetrahydrofurane, 1,4-dioxane, acetonitrile or toluene at temperatures between −50° C. and 120° C., but preferably between −20° C. and 80° C.

The present invention also relates to intermediates (including their salts, stereoisomers and salts of these stereoisomers), methods and processes which are disclosed herein and which are useful in synthesizing final compounds according to this invention. Thus, the present invention also relates to processes disclosed herein for preparing compounds according to this invention, which processes may be performed as described herein. Said processes may comprise one or more steps of converting and/or reacting the mentioned intermediates with the appropriate reaction partners, suitably under conditions as disclosed herein.

Moreover, the compounds of general formula I or intermediates in the synthesis of compounds of general formula I obtained may be resolved into their enantiomers and/or diastereomers, as mentioned hereinbefore. Thus, for example, cis/trans mixtures may be resolved into their cis and trans isomers, and racemic compounds may be separated into their enantiomers.

Thus, for example, the cis/trans mixtures may be resolved by chromatography into the cis and trans isomers thereof. The compounds of general formula I or intermediates in the synthesis of compounds of general formula I, which occur as racemates may be separated by methods known per se (cf. Allinger N. L. and Eliel E. L. in "Topics in Stereochemistry", Vol. 6, Wiley Interscience, 1971) into their optical antipodes and compounds of general formula I or intermediates in the synthesis of compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

Moreover, the compounds of formula I may be converted into the salts thereof, particularly for pharmaceutical use into the pharmaceutically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid. Corresponding processes are known for the skilled person.

When one of the final steps (e.g. removing an acid- or base-labile protecting group from a suitable precursor) or purification is carried out under the presence of an inorganic or organic acid (e.g. hydrochloric, trifluoroacetic, acetic or formic acid or the like) or a base, the compounds of formula I may be obtained—depending on their individual chemical nature and the individual nature of the acid or base used—as free compound or containing said acid or base in an stoechiometric or non-stoechiometric quantity (e.g. as a salt). The acid/base contained can be analyzed according to art-known procedures, e.g. by titration or NMR, and, optionally, removed according to procedures familiar to the skilled person.

Optionally, salts of the compounds of the formula I may be converted into the free compounds. Corresponding processes are known to the skilled person, e.g. via neutralization.

Salts can be obtained by combining or reacting the free compounds with the desired acids or bases, e.g. by dissolving or suspending the free compound in a suitable solvent (e.g. a ketone, such as acetone, methyl ethyl ketone or methyl isobutyl ketone, an ether, such as diethyl ether, diisopropyl ether, tetrahydrofuran or 1,4-dioxane, a chlorinated hydrocarbon, such as methylene chloride or chloroform, a low-molecular-weight aliphatic alcohol, such as methanol, ethanol or isopropanol, or an ester, such as ethyl acetate, or water, or a mixture thereof) which contains the desired acid or base, or to which the desired acid or base is then added. The salts can be obtained by filtering, reprecipitating, precipitating with a nonsolvent for the addition salt or by evaporating the solvent. Salts obtained can be converted to another, e.g. by reaction with an appropriate acid or base or by means of a suitable ion exchanger. Likewise, salts obtained can be converted into the free compounds, which can in turn be converted into salts, by alkalization or by acidification. In this manner, pharmaceutically unacceptable salts can be converted into pharmaceutically acceptable salts.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

The compounds according to the invention are advantageously obtainable using the methods described in the examples that follow, which may also be combined for this purpose with methods known to the skilled person from his/her expert knowledge. Likewise, further compounds according to this invention, whose preparation are not explicitly described in the following examples, can be prepared analogously or similarly to the examples.

Any or all of the compounds according to the present invention which are mentioned as final compounds in the following examples, including the salts, stereoisomers and salts of the stereoisomers thereof, are a particularly interesting subject within the present invention.

Other features and advantages of the present invention will become apparent from the following examples. The following examples serve to illustrate, by way of example, the principles of the invention without restricting it.

EXAMPLES

The following examples serve to further explain the invention without restricting it.

The hereinafter described compounds have been characterized through their characteristic mass after ionisation in a mass-spectrometer, their $R_f$-Value on thin-layer-chromatography plate and/or their retention time on an analytical HPLC.

HPLC Methods:

Method 1: Column: Waters XBridge C18, 30×3.0 mm, 2.5 μm, 60° C.; UV-Detection: 190-400 nm; Eluent A: Water (0.2% Trifluoroacetic acid), Eluent B: Methanol Gradient:

| Time (min.) | % Eluent B | Flow [ml/min] |
| --- | --- | --- |
| 0.00 | 5 | 2.2 |
| 0.05 | 5 | 2.2 |
| 1.40 | 100 | 2.2 |
| 1.80 | 100 | 2.2 |

Method 2: Column: Waters XBridge C18, 30×3.0 mm, 2.5 μm, 60° C.; UV-Detection: 190-400 nm; Eluent A: Water (0.2% Trifluoroacetic acid), Eluent B: Methanol Gradient:

| Time (min.) | % Eluent B | Flow [ml/min] |
| --- | --- | --- |
| 0.00 | 5 | 2.0 |
| 0.20 | 5 | 2.0 |
| 1.50 | 100 | 2.0 |
| 1.55 | 100 | 2.6 |
| 1.75 | 100 | 2.6 |

Method 3: Column: Waters XBridge C18, 30×4.6 mm, 3.5 μm, 60° C.; UV-Detection: 190-400 nm; Eluent A: Water (0.2% Trifluoroacetic acid), Eluent B: Methanol Gradient:

| Time (min.) | % Eluent B | Flow [ml/min] |
| --- | --- | --- |
| 0.00 | 5 | 4.0 |
| 0.15 | 5 | 4.0 |
| 1.70 | 100 | 4.0 |
| 2.25 | 100 | 4.6 |

Method 4: Column: Merck Chromolith Flash RP18e, 25×4.6 mm, 2 μm, UV-Detection: 230 nm/254 nm; Eluent A: Water (0.1% Formic acid), Eluent B: Methanol Gradient:

| Time (min.) | % Eluent B | Flow [ml/min] |
| --- | --- | --- |
| 0.00 | 10 | 2.5 |
| 1.61 | 100 | 2.5 |
| 2.25 | 100 | 2.5 |

Method 5: Column: Agilent Stable Bond SB-C18, 30×4.6 mm, 1.8 μm; UV-Detection: DAD 190-400 nm; Eluent A: Water (0.1% Trifluoacetic acid), Eluent B: Methanol Gradient:

| Time (min.) | % Eluent B | Flow [ml/min] |
| --- | --- | --- |
| 0.00 | 10 | 3.0 |
| 1.80 | 100 | 3.0 |
| 2.00 | 100 | 3.0 |
| 2.15 | 10 | 3.0 |
| 2.35 | 10 | 3.0 |

Thin layer chromatography: Merck; TLC Silica gel 60 $F_{254}$

Preparation of the Starting Compounds

Intermediate 1

7-Aminospiro[2.5]non-6-en-5-one

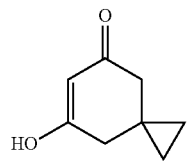

Step 1: 1-Cyclopropylidenepropan-2-one

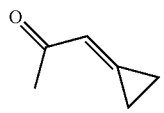

A mixture of 219 g 1-(triphenylphosphoraniliden)-2-propanone 100 g (1-Ethoxy-cyclopropoxy)-trimethyl-silane and 13.1 g para-toluenesulfonic acid in 280 ml 1,2-Dichlorobenzene is heated in an autoclave to 105° C. for 5 hours. The this mixture was cooled to room temperature and stirred for 18 hours. The product is purified by distillation.

Yield: 350 g of a 7% solution (based on 1H-NMR) in 1,2-dichlorobenzene (44% of theory)

Step 2: 7-Hydroxyspiro[2.5]oct-6-en-5-one

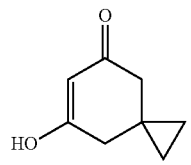

5.75 g Sodium added in portions to 240 ml of methanol and the solution is heated to reflux for 1 hour. 28.4 ml Dimethylmalonate are added and the mixture is heated to reflux for another 10 minutes. The mixture is cooled to 35° C., 350 g 1-cyclobutylidenepropan-2-one (7% in 1,2-dichlorobenzene) are added and the mixture is refluxed for 1 hour. After recooling to room temperature a solution of 28.0 g potassium hydroxide in 130 ml water are added and the mixture is refluxed for 1 hour. The mixture is cooled to room temperature, the pH is adjusted to 1.5 by careful addition of half saturated hydrochloric acid and it is refluxed for 1 hour. The mixture is cooled to room temperature and the aqueous phase is extracted with ethyl acetate. The combined organic phases are dried over sodium sulfate, concentrated in vacuo and the residue is purified by chromatography on silica gel (petroleum ether/ethyl acetate 50:50).

Yield: 10.0 g (28% of theory)

Step 3: 7-Aminospiro[2.5]non-6-en-5-one

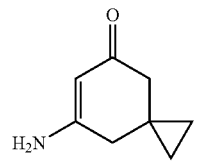

15 g 7-Hydroxy-spiro[2.5]oct-6-en-5-one and 10.9 g ammonium acetate are dissolved in 170 ml toluene and 1.9 ml acetic acid. The mixture is refluxed for 4 hours using a Dean-Stark trap. After cooling to room temperature 100 ml of tert.-butyl methyl ether are added, the precipitated product is collected by filtration and dried at 50° C. in vacuo.

Yield: 13.9 g (93% of theory)
Mass spectrometry (ESI$^+$): m/z=138 [M+H]$^+$
HPLC (Method 1): Retention time=0.430 min.

Intermediate 2

(S)-9-(tert-Butyldimethylsilyloxy)-4-isopropyl-9-hydroxy-,7,7-(ethan-1,2-diyl)-2',3',5',6,6',7,8,9-octahydro-3H-spiro[furo[3,4-c]quinoline-1,4'-pyran]-3-one

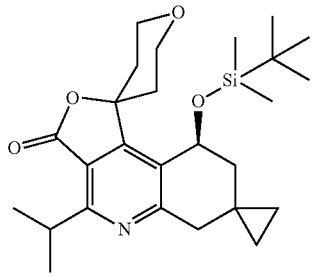 [SMILES: CC(C)c1nc2c(c3c1C(=O)OC31CCOCC1)[C@@H](O[Si](C)(C)C(C)(C)C)CC1(CC1)C2]

Step 1: 1,6-Dioxaspiro[2.5]octane

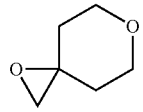

Under nitrogen 6.6 g sodiumhydride (60% in mineral oil) are suspended in 90 ml tetrahydrofurane and cooled to 0° C.

91.7 Trimethylsulfonium iodide are added in portions. To this mixture a solution of 15 g dihydro-2H-pyran-4(3H)-one in 300 ml dimethylsulfoxide and 60 ml tetrahydrofurane is added dropwise. Afterwards the mixture is warmed to room temperature and stirred for 18 hours. The mixture is then poured into 1.2 l icewater and extracted for three times with diethylether. The combined organic phases are washed with brine and dried with sodium sulphate. Evaporation of the solvents in vacuo gives the product.

Yield: 10.15 g (59% of theory)
R$_f$-value: 0.47 (silica gel, petrole ether/ethylacetate 1:1)

Step 2: 3-Isobutyryl-1,8-dioxaspiro[4.5]decan-2-one

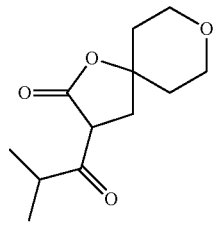 [SMILES: CC(C)C(=O)C1CC2(CCOCC2)OC1=O]

6.6 g 1,6-Dioxaspiro[2.5]octane and 8.2 ml methyl 4-methyl-3-oxopentanoate are dissolved in 30 ml ethanol, cooled to 0° C. and treated in portions with 3.9 g sodium ethoxide. After completion of the addition the mixture is warmed to room temperature and stirred for 18 hours. Then the mixture is poured in 200 ml ice water, acidified to pH 3 by addition of 1 M hydrochloric acid and extracted for three times with ethylacetate. The combined organic phases are dried with sodium sulphate and the solvents are evaporated in vacuo. The residue is chromatographed on silica gel (petrole ether/ethylacetate 100:0 to 50:50).

Yield: 3.93 g (33% of theory)
Mass spectrometry (ESI$^+$): m/z=227 [M+H]$^+$
HPLC (Method 4): Retention time=0.952 min.

Step 3: 3-Isobutyryl-1,8-dioxaspiro[4.5]dec-3-en-2-one

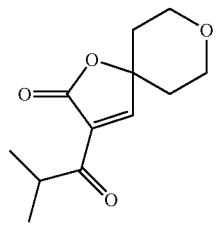 [SMILES: CC(C)C(=O)C1=CC2(CCOCC2)OC1=O]

2.16 g 4-Methoxypyridine-1-oxide hydrate and 5.57 g 2-iodoxybenzoic acid (45 wt-%) are suspended in 20 ml dimethylsulfoxide and stirred for 20 minutes until all material has dissolved. Then 3.0 g 3-isobutyryl-1,8-dioxaspiro[4.5]decan-2-one are added and the mixture is stirred for 24 hours. The mixture is diluted with saturated solution of sodium bicarbonate in water and the formed precipitate is filtered off. The mother liquour is extracted for three times with ethylacetate. The combined organic phases are dried with sodium sulphate and the solvents are evaporated in vacuo. The residue is chromatographed on silica gel (petrole ether/ethylacetate 100:0 to 40:60).

Yield: 1.0 g (34% of theory)
Mass spectrometry (ESI$^+$): m/z=225 [M+H]$^+$
HPLC (Method 4): Retention time=0.899 min.

Step 4: 4-Isopropyl-7,7-(ethan-1,2-diyl)-2',3',5',6',7,8-hexahydro-3H-spiro[furo[3,4-c]quinoline-1,4'-pyran]-3,9(6H)-dione

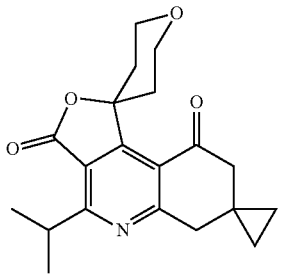 [SMILES: CC(C)c1nc2c(c3c1C(=O)OC31CCOCC1)C(=O)CC1(CC1)C2]

8.0 g 3-Isobutyryl-1,8-dioxaspiro[4.5]dec-3-en-2-one and 7.4 g 7-Amino-spiro[2.5]oct-6-en-5-one are mixed and heated to 200° C. for 10 minutes under a vacuo of 20 mbar. The mixture is cooled to room temperature, 50 ml ethylacetate are added, the mixture is stirred for 60 minutes and the precipitate is isolated by filtration. The crude product is dissolved in 100 ml dichloromethane, treated with 7.9 g 2,3-dichloro-5,6-dicyano-p-benzoquinone and stirred for 4 hours. The precipitate is isolated by filtration, dissolved in dichloromethane and washed with saturated aqueous sodium-bicarbonate solution. The phases are separated, the organic phase is dried with sodium sulphate and the solvents are evaporated in vacuo.

Yield: 6.7 g (58% of theory)
Mass spectrometry (ESI$^+$): m/z=342 [M+H]$^+$
HPLC (Method 2): Retention time=1.234 min.

Step 5: (S)-4-Isopropyl-9-hydroxy-,7,7-(ethan-1,2-diyl)-2',3',5',6,6',7,8,9-octahydro-3H-spiro[furo[3,4-c]quinoline-1,4'-pyran]-3-one

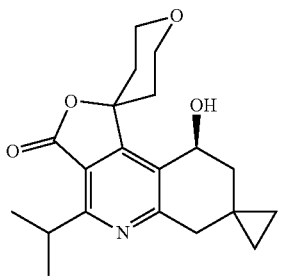 [SMILES: CC(C)c1nc2c(c3c1C(=O)OC31CCOCC1)[C@@H](O)CC1(CC1)C2]

132 mg (1R,2S)-(+)-cis-1-Amino-2-indanol are dissolved in 300 ml tetrahydrofurane and to this solution are dropwise added 2.19 ml of a borane-diethylaniline-complex. After completion of gas evolution the solution is cooled to 0° C. and 2 g 4-Isopropyl-7,7-(ethan-1,2-diyl)-2',3',5',6',7,8-hexahydro-3H-spiro[furo[3,4-c]quinoline-1,4'-pyran]-3,9(6H)-dione in 10 ml tetrahydrofurane are added dropwise. The temperature is raised during 2 hours to room temperature and the mixture is stirred for 18 hours, 100 mg (1R,2S)-(+)-cis-1-Amino-2-indanol are added and stirring is continued for further 7 hours. 20 ml methanol are added dropwise and the mixture is stirred for additional 30 minutes. The solvents are evaporated in vacuo and the residue is chromatographed on silica gel (petrole ether/ethylacetate 100:0 to 0:100).

Yield: 1.51 g (75% of theory)
Mass spectrometry (ESI$^+$): m/z=344 [M+H]$^+$
HPLC (Method 1): Retention time=1.137 min.

Step 6: (S)-9-(tert-Butyldimethylsilyloxy)-4-isopropyl-9-hydroxy-,7,7-(ethan-1,2-diyl)-2',3',5',6,6',7,8,9-octahydro-3H-spiro[furo[3,4-c]quinoline-1,4'-pyran]-3-one

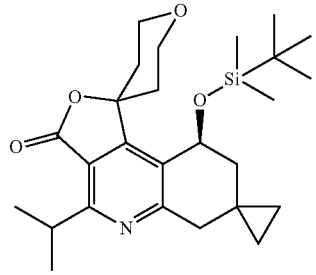 [SMILES: CC(C)c1nc2c(c3c1C(=O)OC31CCOCC1)[C@@H](O[Si](C)(C)C(C)(C)C)CC1(CC1)C2]

1.50 g (S)-4-Isopropyl-9-hydroxy-,7,7-(ethan-1,2-diyl)-2',3',5',6,6',7,8,9-octahydro-3H-spiro[furo[3,4-c]quinoline-1,4'-pyran]-3-one are dissolved in 15 ml tetrahydrofurane 1.64 ml 2,6-lutidine and 3.07 ml trifluoromethanesulfonic acid-tert.-butyldimethylsilylester are added dropwise and the mixture is stirred for 1 hour. Then the solvents are evaporated in vacuo and the residue is chromatographed on silica gel (petrole ether/ethylacetate 100:0 to 0:100).

Yield: 1.92 g (96% of theory)
Mass spectrometry (ESI$^+$): m/z=458 [M+H]$^+$
HPLC (Method 1): Retention time=1.543 min Intermediate 3

5-Iodo-2-(trifluoromethyl)benzonitrile

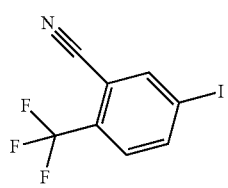 [SMILES: N#Cc1cc(I)ccc1C(F)(F)F]

In a microwave vial 2.24 g 5-bromo-2-(trifluoromethyl)benzonitrile are dissolved in 10 ml 1,4-dioxane. 90 mg copper-(I)-iodide and 2.7 g sodium iodide are added and the mixture is purged for 5 minutes with argon. 142 µl trans-N,N'-dimet6hylcyclohexane-1,2-diamine and 1.9 ml hexamethyldisilazane are added and the mixture is heated for 6 hours to 110° C. The mixture is diluted in 100 ml 4 M hydrochloric acid and stirred for 10 minutes. This aqueous phase is three times extracted with dichloromethane. The combined organic phases are washed with brine and dried with magnesium sulphate. The solvents are evaporated in vacuo and the residue is chromatographed on silica gel (cyclohexane/ethylacetate 85:15).

Yield: 2.35 g (88% of theory)
HPLC (Method 5): Retention time=1.288 min.

Intermediate 4

(9S)-9-(tert-Butyldimethylsilyloxy)-4-isopropyl-9-hydroxy-,7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]-3-ol

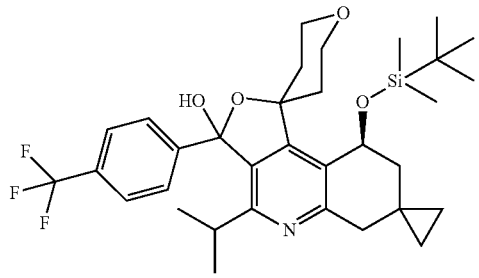 [SMILES: CC(C)c1nc2c(c3c1C(O)(c1ccc(C(F)(F)F)cc1)OC31CCOCC1)[C@@H](O[Si](C)(C)C(C)(C)C)CC1(CC1)C2]

3.66 g 1-Iodo-4-(trifluoromethyl)benzene are dissolved in 40 ml tetrahydrofurane, cooled to −78° C. and treated dropwise with 15.6 ml of a 1.7 M solution of tert.-butyllithium in n-pentan. The mixture is stirred for 5 minutes and then a solution of 4.00 g (S)-4-Isopropyl-9-hydroxy-,7,7-(ethan-1,2-diyl)-2',3',5',6,6',7,8,9-octahydro-3H-spiro[furo[3,4-c]quinoline-1,4'-pyran]-3-one in 20 ml tetrahydrofurane is added dropwise. The mixture is stirred for 45 minutes at −78° C., then quenched by addition of saturated aqueous ammonium chloride solution and the aqueous phase is extracted with ethyl acetate. The combined organic phases are dried with sodium sulphate and the solvents are evaporated in vacuo. The residue is chromatographed on silica gel (petrole ether/ethylacetate 100:0 to 70:30).

Yield: 3.35 mg (63% of theory)
Mass spectrometry (ESI$^+$): m/z=604 [M+H]$^+$
HPLC (Method 1): Retention time=1.466 and 1,505 min. (Diastereomers)

Analogously to above Intermediate 4 the following intermediates are obtained:

(1) 5-((9S)-9-(tert-butyldimethylsilyloxy)-3-hydroxy-4-isopropyl-7,7-(ethan-1,2-diyl)-2',3',5',6,6',7,8,9-octahydro-3H-spiro[furo[3,4-c]quinoline-1,4'-pyran]-3-yl)-2-(trifluoromethyl)benzonitrile

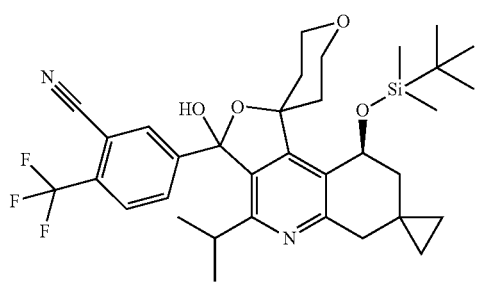 [SMILES: CC(C)c1nc2c(c3c1C(O)(c1ccc(C(F)(F)F)c(C#N)c1)OC31CCOCC1)[C@@H](O[Si](C)(C)C(C)(C)C)CC1(CC1)C2]

Obtained by starting from 5-Iodo-2-trifluoromethyl-benzonitrile.

Mass spectrometry (ESI$^+$): m/z=629 [M+H]$^+$
HPLC (Method 1): Retention time=1.492 and 1,519 min.
Rf-value: 0.23 and 0.46 (silica gel, petrole ether/ethylacetate 8:2)

(2) (3R,9S)-9-(tert-butyldimethylsilyloxy)-4-isopropyl-7,7-(ethan-1,2-diyl)-3-(3-methoxy-4-(trifluoromethyl)phenyl)-2',3',5',6,6',7,8,9-octahydro-3H-spiro[furo[3,4-c]quinoline-1,4'-pyran]

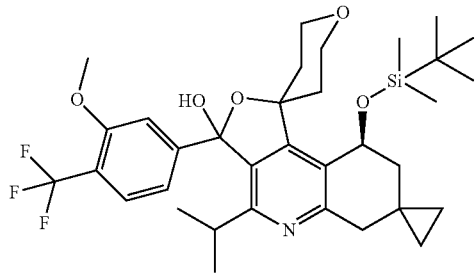 [SMILES: COc1cc(C2(O)OC3(CCOCC3)c3c4c(nc(C(C)C)c32)CC2(CC2)C[C@@H]4O[Si](C)(C)C(C)(C)C)ccc1C(F)(F)F]

Obtained by starting from 4-Iodo-2-methoxy-1-trifluoromethyl-benzene

Mass spectrometry (ESI⁺): m/z=618 [M+H]⁺

HPLC (Method 1): Retention time=1.470 and 1,506 min.

(3) (3R,9S)-9-(tert-butyldimethylsilyloxy)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]

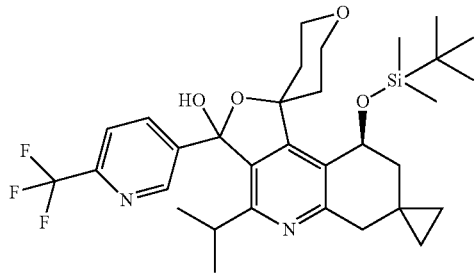 [SMILES: CC(C)c1nc2c(c3c1C(O)(c1ccc(C(F)(F)F)nc1)OC31CCOCC1)[C@@H](O[Si](C)(C)C(C)(C)C)CC1(CC1)C2]

Obtained by starting from 5-Iodo-2-trifluoromethyl-pyridine

Mass spectrometry (ESI⁺): m/z=605 [M+H]⁺

HPLC (Method 1): Retention time=1.462 and 1,494 min.

Intermediate 5

(3R,9S)-9-(tert-Butyldimethylsilyloxy)-4-isopropyl-9-hydroxy-,7,7-(ethan-1,2-diyl)-3-(4-(trifluoromethyl)phenyl)-2',3,5',6,6,7,8,9-octahydro-3H-spiro[furo[3,4-c]quinoline-1,4'-pyran]

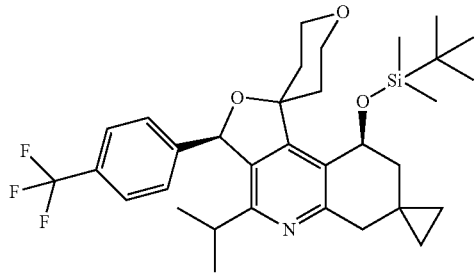 [SMILES: CC(C)c1nc2c(c3c1[C@@H](c1ccc(C(F)(F)F)cc1)OC31CCOCC1)[C@@H](O[Si](C)(C)C(C)(C)C)CC1(CC1)C2]

and (3S,9S)-9-(tert-Butyldimethylsilyloxy)-4-isopropyl-9-hydroxy-,7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]

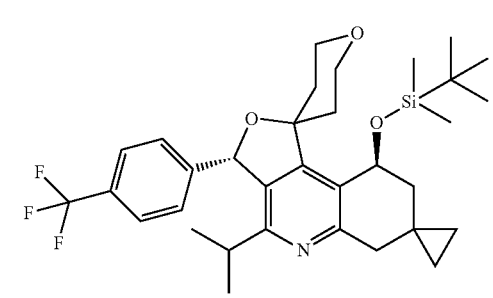 [SMILES: CC(C)c1nc2c(c3c1[C@H](c1ccc(C(F)(F)F)cc1)OC31CCOCC1)[C@@H](O[Si](C)(C)C(C)(C)C)CC1(CC1)C2]

3.,35 g (9S)-9-(tert-butyldimethylsilyloxy)-4-isopropyl-9-hydroxy-7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]-3-ol are dissolved in 100 ml dichloromethane, cooled to 0° C. and treated dropwise with 22.5 ml of a 1 m solution of titanium-(IV)-chloride in dichloromethane. The mixture is stirred for 30 minutes at room temperature and 6.26 g sodiumtriacetoxyborohydride are added. The mixture is stirred for 2 hours at room temperature and then quenched with saturated aqueous sodium bicarbonate solution. The aqueous phase is extracted with dichloromethane and the combined organic phases are dried with sodium sulphate. The solvents are evaporated in vacuo and the residue is chromatographed on silica gel (petrole ether/ethylacetate 100:0 to 85:15).

(3R,9S)-9-(tert-butyldimethylsilyloxy)-4-isopropyl-9-hydroxy-,7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]

Yield: 1.77 g (54% of theory)

Mass spectrometry (ESI⁺): m/z=588 [M+H]⁺

HPLC (Method 1): Retention time=1.956 min.

R_f-value: 0.43 (silica gel, petrole ether/ethylacetate 9:1)

(3S,9S)-9-(tert-butyldimethylsilyloxy)-4-isopropyl-9-hydroxy-,7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]

Yield: 1.03 g (32% of theory)

Mass spectrometry (ESI⁺): m/z=588 [M+H]⁺

HPLC (Method 1): Retention time=1.956 min.

R_f-value: 0.28 (silica gel, petrole ether/ethylacetate 9:1)

Analogously to Intermediate 5 the following intermediates are obtained:

(1) 5-((3R,9S)-9-(tert-butyldimethylsilyloxy)-4-isopropyl-7,7-(ethan-1,2-diyl)-2',3',5',6,6',7,8,9-octahydro-3H-spiro[furo[3,4-c]quinoline-1,4'-pyran]-3-yl)-2-(trifluoromethyl)benzonitrile

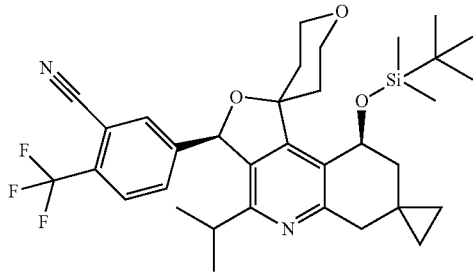 [SMILES: CC(C)c1nc2c(c3c1[C@@H](c1ccc(C(F)(F)F)c(C#N)c1)OC31CCOCC1)[C@@H](O[Si](C)(C)C(C)(C)C)CC1(CC1)C2]

Mass spectrometry (ESI⁺): m/z=613 [M+H]⁺
HPLC (Method 1): Retention time=1.528 min.
Rf-value: 0.20 (silica gel, petrole ether/ethylacetate 9:1)
and 5-((3S,9S)-9-(tert-butyldimethylsilyloxy)-4-isopropyl-7,7-(ethan-1,2-diyl)-2',3',5',6,6',7,8,9-octahydro-3H-spiro[furo[3,4-c]quinoline-1,4'-pyran]-3-yl)-2-(trifluoromethyl)benzonitrile

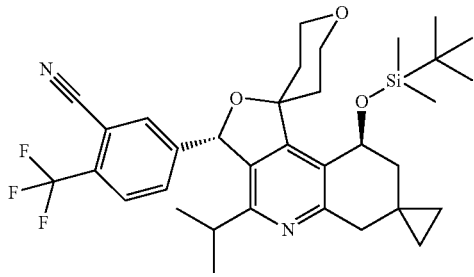 [SMILES: CC(C)c1nc2c(c3c1[C@H](c1ccc(C(F)(F)F)c(C#N)c1)OC31CCOCC1)[C@@H](O[Si](C)(C)C(C)(C)C)CC1(CC1)C2]

Mass spectrometry (ESI⁺): m/z=613 [M+H]⁺
HPLC (Method 1): Retention time=1.528 min.
Rf-value: 0.32 (silica gel, petrole ether/ethylacetate 9:1)
Obtained by starting from 5-((9S)-9-(tert-butyldimethylsilyloxy)-3-hydroxy-4-isopropyl-7,7-(ethan-1,2-diyl)-2',3',5',6,6',7,8,9-octahydro-3H-spiro[furo[3,4-c]quinoline-1,4'-pyran]-3-yl)-2-(trifluoromethyl)benzonitrile.

(2) (3R,9S)-9-(tert-butyldimethylsilyloxy)-4-isopropyl-7,7-(ethan-1,2-diyl)-3-(3-methoxy-4-(trifluoromethyl)phenyl)-2',3',5',6,6',7,8,9-octahydro-3H-spiro[furo[3,4-c]quinoline-1,4'-pyran]

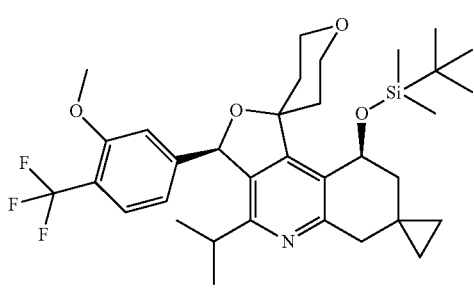 [SMILES: COc1cc([C@H]2OC3(CCOCC3)c3c2c(C(C)C)nc2c3[C@@H](O[Si](C)(C)C(C)(C)C)CC3(CC3)C2)ccc1C(F)(F)F]

Mass spectrometry (ESI⁺): m/z=618 [M+H]⁺
HPLC (Method 1): Retention time=1.525 min.
Rf-value: 0.18 (silica gel, petrole ether/ethylacetate 9:1)
and (3S,9S)-9-(tert-butyldimethylsilyloxy)-4-isopropyl-7,7-(ethan-1,2-diyl)-3-(3-methoxy-4-(trifluoromethyl)phenyl)-2',3',5',6,6',7,8,9-octahydro-3H-spiro[furo[3,4-c]quinoline-1,4'-pyran]

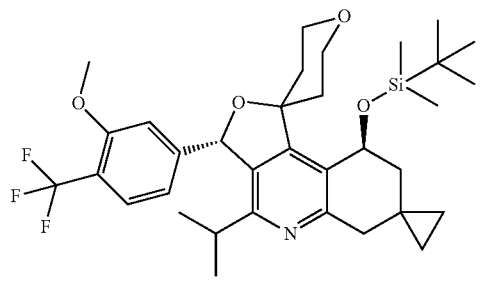 [SMILES: COc1cc([C@@H]2OC3(CCOCC3)c3c2c(C(C)C)nc2c3[C@@H](O[Si](C)(C)C(C)(C)C)CC3(CC3)C2)ccc1C(F)(F)F]

Mass spectrometry (ESI⁺): m/z=618 [M+H]+
HPLC (Method 1): Retention time=1.525 min.
Rf-value: 0.31 (silica gel, petrole ether/ethylacetate 9:1)
Obtained by starting from (9S)-9-(tert-butyldimethylsilyloxy)-4-isopropyl-7,7-(ethan-1,2-diyl)-3-(3-methoxy-4-(trifluoromethyl)phenyl)-2',3',5',6,6',7,8,9-octahydro-3H-spiro[furo[3,4-c]quinoline-1,4'-pyran]-3-ol.

(3) (3R,9S)-9-(tert-butyldimethylsilyloxy)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]

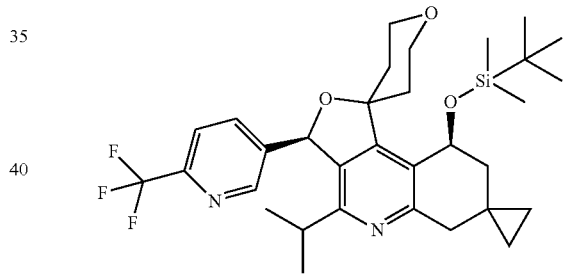

Mass spectrometry (ESI⁺): m/z=589 [M+H]⁺
HPLC (Method 1): Retention time=1.598 min.
Rf-value: 0.12 (silica gel, petrole ether/ethylacetate 9:1)
and (3S,9S)-9-(tert-butyldimethylsilyloxy)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]

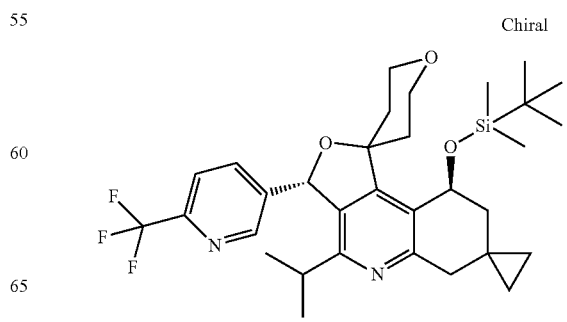

Mass spectrometry (ESI⁺): m/z=589 [M+H]⁺
HPLC (Method 1): Retention time=1.598 min.
Rf-value: 0.22 (silica gel, petrole ether/ethylacetate 9:1)
Obtained by starting from (9S)-9-(tert-butyldimethylsilyloxy)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]-3-ol.

Intermediate 6

(3R,6RS,9S)-9-(tert-butyldimethylsilyloxy)-4-isopropyl-7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]-6-yl acetate

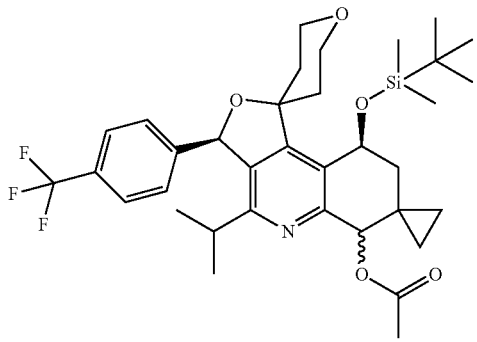 [SMILES: CC(=O)OC1c2nc(C(C)C)c3c(c2[C@@H](O[Si](C)(C)C(C)(C)C)CC12CC2)C1(CCOCC1)O[C@@H]3c1ccc(C(F)(F)F)cc1]

70 mg (3R,9S)-9-(tert-butyldimethylsilyloxy)-4-isopropyl-9-hydroxy-,7,7-(ethan-1,2-diyl)-3-(4-(trifluoromethyl)phenyl)-2',3',5',6,6',7,8,9-octahydro-3H-spiro[furo[3,4-c]quinoline-1,4'-pyran] are dissolved in 2 ml dichloromethane and treated with 67.5 mg of meta-chlorperbenzoic acid (MCPBA) (70%). The mixture is stirred for 18 hours and then partitioned between dichloromethane and a solution of sodium hydroxide in water (1M). The organic phase is dried with sodium sulphate the solvents are evaporated.

The residue is dissolved in 2 ml acetic acid anhydride and heated for 2 hours at 130° C. Excess acetic acid anhydride is removed in vacuo and the residue is diluted with diethylether. After washing with saturated aqueous sodium bicarbonate the organic phase is dried with sodium sulphate. The solvent is evaporated in vacuo and the residue is purified by reversed phase column chromatograpy (Xbridge 10 μM, water (0.1% trifluoroacetic acid)/methanol 90:10 to 0:100).
(Yield: 37 mg (49% of theory)
Mass spectrometry (ESI⁺): m/z=646 [M+H]⁺
HPLC (Method 1): Retention time=1.584 min.
Analogously to Intermediate 6 the following intermediates are obtained:

(1) (3R,6RS,9S)-9-(tert-butyldimethylsilyloxy)-3-(3-cyano-4-(trifluoromethyl)phenyl)-4-isopropyl-7,7-(ethpan-1,3-diyl)-2',3',5',6,6',7,8,9-octahydro-3H-spiro[furo[3,4-c]quinoline-1,4'-pyran]-6-yl acetate

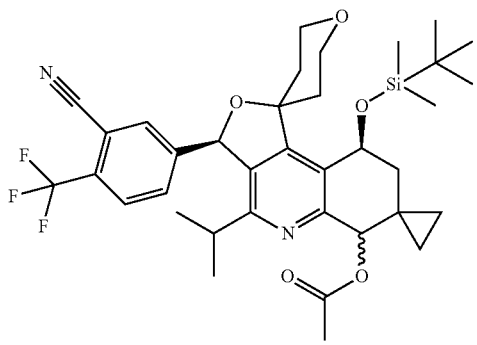 [SMILES: CC(=O)OC1c2nc(C(C)C)c3c(c2[C@@H](O[Si](C)(C)C(C)(C)C)CC12CC2)C1(CCOCC1)O[C@@H]3c1ccc(C(F)(F)F)c(C#N)c1]

Obtained by starting from (3R,9S)-9-(tert-butyldimethylsilyloxy)-3-(3-cyano-4-(trifluoromethyl)phenyl)-4-isopropyl-7,7-(ethan-1,2-diyl)-2',3',5',6,6',7,8,9-octahydro-3H-spiro[furo[3,4-c]quinoline-1,4'-pyran].
Mass spectrometry (ESI⁺): m/z=671 [M+H]⁺
HPLC (Method 3): Retention time=1.998 min.

(2) (3R,6RS,9S)-9-(tert-butyldimethylsilyloxy)-3-(3-methoxy-4-(trifluoromethyl)phenyl)-4-isopropyl-7,7-(ethpan-1,3-diyl)-2',3',5',6,6',7,8,9-octahydro-3H-spiro[furo[3,4-c]quinoline-1,4'-pyran]-6-yl acetate

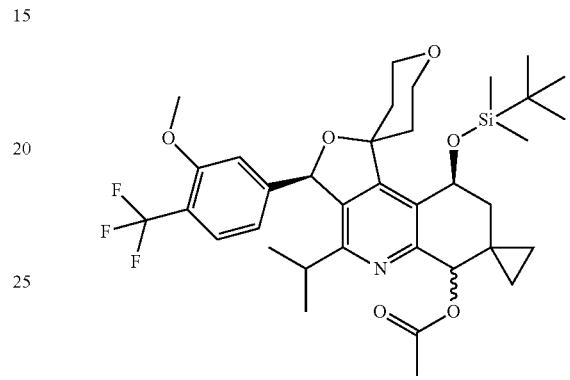

Obtained by starting from (3R,9S)-9-(tert-butyldimethylsilyloxy)-3-(3-methoxy-4-(trifluoromethyl)phenyl)-4-isopropyl-7,7-(ethan-1,2-diyl)-2',3',5',6,6',7,8,9-octahydro-3H-spiro[furo[3,4-c]quinoline-1,4'-pyran].
Mass spectrometry (ESI⁺): m/z=676 [M+H]⁺
HPLC (Method 1): Retention time=1.566 min.

(3) (3R,6RS,9S)-9-(tert-butyldimethylsilyloxy)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]-6-yl acetate

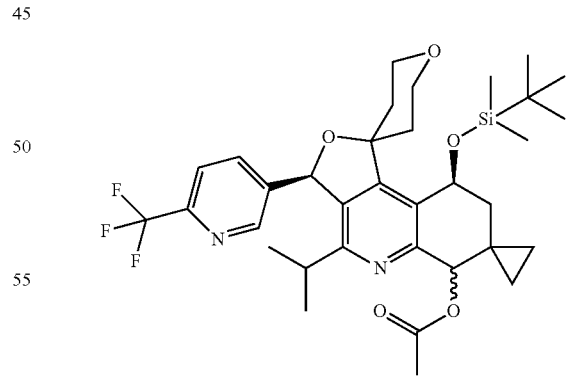

Obtained by starting from (3R,9S)-9-(tert-butyldimethylsilyloxy)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran].
Mass spectrometry (ESI⁺): m/z=647 [M+H]⁺
HPLC (Method 1): Retention time=1.528 min.

Preparation of the Final Compounds

Examples 1-4

(1) (3R,9S)-4-isopropyl-7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]-9-ol (example 1)

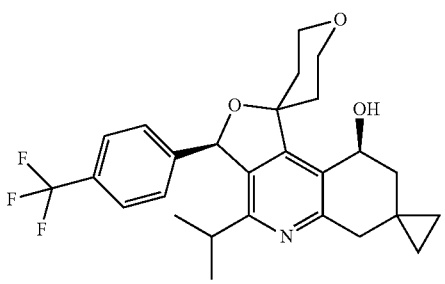 [SMILES: CC(C)c1nc2c(c3c1[C@@H](c1ccc(C(F)(F)F)cc1)OC31CCOCC1)[C@@H](O)CC1(CC1)C2]

To a solution of 1.77 g (3R,9S)-9-(tert-Butyldimethylsilyloxy)-4-isopropyl-9-hydroxy-,7,7-(ethan-1,2-diyl)-3-(4-(trifluoromethyl)phenyl)-2',3',5',6,6',7,8,9-octahydro-3H-spiro[furo[3,4-c]quinoline-1,4'-pyran] in 20 ml tetrahydrofurane are added 3.41 ml of a 1 M solution of tetrabutylammonium fluoride in tetrahydrofurane. The solution is stirred for 3 hours at room temperature, then the solvent is evaporated in vacuo and the residue is chromatographed on silica gel (cyclohexane/ethylacetate 90:10 to 50:50).

Yield: 1.34 g (94% of theory)

Mass spectrometry (ESI$^+$): m/z=474 [M+H]$^+$

HPLC (Method 1): Retention time=1.160 min.

Analogously to example 1 the following examples are obtained:

(2) 5-((3R,9S)-9-hydroxy-4-isopropyl-7,7-dimethyl-2',3',5',6,6',7,8,9-octahydro-3H-spiro[furo[3,4-c]quinoline-1,4'-pyran]-3-yl)-2-(trifluoromethyl)benzonitrile (example 2)

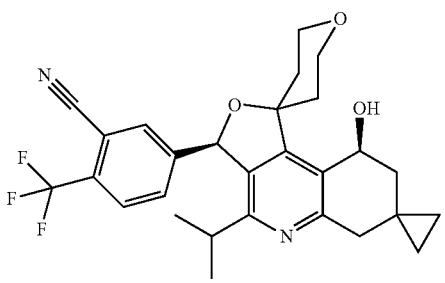 [SMILES: CC(C)c1nc2c(c3c1[C@@H](c1ccc(C(F)(F)F)c(C#N)c1)OC31CCOCC1)[C@@H](O)CC1(CC1)C2]

Obtained by starting from 5-((3R,9S)-9-(tert-butyldimethylsilyloxy)-4-isopropyl-7,7-(ethan-1,2-diyl)-2',3,5,6,6',7,8,9-octahydro-3H-spiro[furo[3,4-c]quinoline-1,4'-pyran]-3-yl)-2-(trifluoromethyl)benzonitrile.

Mass spectrometry (ESI$^+$): m/z=499 [M+H]$^+$

HPLC (Method 1): Retention time=1.142 min.

(3) (3R,9S)-4-isopropyl-7,7-(ethan-1,2-diyl)-3-(3-methoxy-4-(trifluoromethyl)phenyl)-2',3,5',6,6',7,8,9-octahydro-3H-spiro[furo[3,4-c]quinoline-1,4'-pyran]-9-ol (example 3)

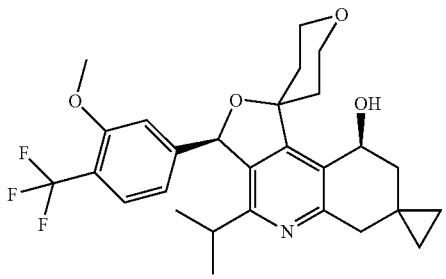 [SMILES: COc1cc([C@H]2OC3(CCOCC3)c3c2c(C(C)C)nc2c3[C@@H](O)CC3(CC3)C2)ccc1C(F)(F)F]

Obtained by starting from (3R,9S)-9-(tert-butyldimethylsilyloxy)-4-isopropyl-7,7-(ethan-1,2-diyl)-3-(3-methoxy-4-(trifluoromethyl)phenyl)-2',3,5',6,6',7,8,9-octahydro-3H-spiro[furo[3,4-c]quinoline-1,4'-pyran] (EXAMPLE 4)

Mass spectrometry (ESI$^+$): m/z=504 [M+H]$^+$

HPLC (Method 1): Retention time=1.160 min.

(4) (3R,9S)-4-isopropyl-7,7-dimethyl-3-(6-(trifluoromethyl)pyridin-3-yl)-2',3,5',6,6',7,8,9-octahydro-3H-spiro[furo[3,4-c]quinoline-1,4'-pyran]-9-ol (example 4)

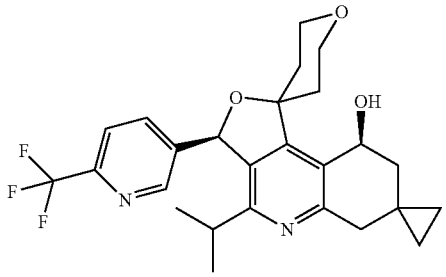 [SMILES: CC(C)c1nc2c(c3c1[C@@H](c1ccc(C(F)(F)F)nc1)OC31CCOCC1)[C@@H](O)CC1(CC1)C2]

Obtained by starting from (3R,9S)-9-(tert-butyldimethylsilyloxy)-4-isopropyl-7,7-(ethan-1,2-diyl)-3-(6-(trifluoromethyl)pyridin-3-yl)-2',3,5',6,6',7,8,9-octahydro-3H-spiro[furo[3,4-c]quinoline-1,4'-pyran]

Mass spectrometry (ESI$^+$): m/z=475 [M+H]$^+$

HPLC (Method 1): Retention time=1.0514 min.

Examples 5-8

(3R,6R,9S)-4-isopropyl-7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]-6,9-diol (example 5)

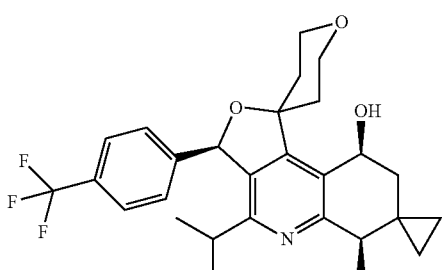

35 mg (3R,6RS,9S)-9-(tert-butyldimethylsilyloxy)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]-6-yl acetate are dissolved in 0.5 ml methanol and treated with 43 mg potassium carbonate. The mixture is stirred for 24 hours at room temperature, diluted with ethyl acetate and washed with brine. The organic phase is dried with sodium sulphate and the solvent is evaporated in vacuo. The residue is purified by revered phasecolumn chromatography (XBridge C18 10 μm, water (0.1% trifluoroacetic acid)/methanol 90:10 to 0:100).

Yield: 14 mg (53% of theory)

Mass spectrometry (ESI$^+$): m/z=490 [M+H]$^+$

HPLC (Method 1): Retention time=1.291 min.

Analogously to example 5 the following examples are obtained:

(1) 5-((3R,6R,9S)-6,9-dihydroxy-4-isopropyl-7,7-(ethan-1,2-diyl)-2',3',5',6,6',7,8,9-octahydro-3H-spiro[furo[3,4-c]quinoline-1,4'-pyran]-3-yl)-2-(trifluoromethyl)benzonitrile (example 6)

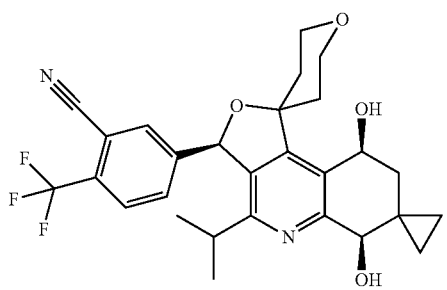 [SMILES: CC(C)c1nc2c(c3c1[C@@H](c1ccc(C(F)(F)F)c(C#N)c1)OC31CCOCC1)[C@@H](O)CC1(CC1)[C@H]2O]

Obtained by starting from (3R,6RS,9S)-9-(tert-butyldimethylsilyloxy)-3-(3-cyano-4-(trifluoromethyl)phenyl)-4-isopropyl-7,7-(ethan-1,2-diyl)-2',3',5',6,6',7,8,9-octahydro-3H-spiro[furo[3,4-c]quinoline-1,4'-pyran]-6-yl acetate.

Mass spectrometry (ESI$^+$): m/z=515 [M+H]$^+$

HPLC (Method 2): Retention time=1.222 min.

(2) (3R,6R,9S)-4-isopropyl-7,7-(ethan-1,2-diyl)-3-(3-methoxy-4-(trifluoromethyl)phenyl)-2',3',5',6,6',7,8,9-octahydro-3H-spiro[furo[3,4-c]quinoline-1,4'-pyran]-6,9-diol (example 7)

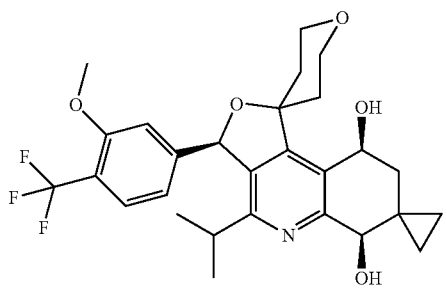 [SMILES: COc1cc([C@H]2OC3(CCOCC3)c3c2c(C(C)C)nc2c3[C@@H](O)CC3(CC3)[C@H]2O)ccc1C(F)(F)F]

Obtained by starting from (3R,6RS,9S)-9-(tert-butyldimethylsilyloxy)-3-(3-methoxy-4-(trifluoromethyl)phenyl)-4-isopropyl-7,7-(ethan-1,2-diyl)-2',3',5',6,6',7,8,9-octahydro-3H-spiro[furo[3,4-c]quinoline-1,4'-pyran]-6-ylacetate.

Mass spectrometry (ESI$^+$): m/z=520 [M+H]$^+$

HPLC (Method 1): Retention time=1.266 min.

(3) (3R,6R,9S)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]-6,9-diol (example 8)

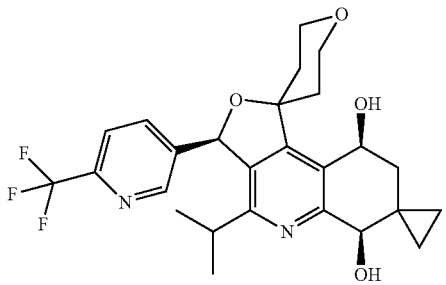 [SMILES: CC(C)c1nc2c(c3c1[C@@H](c1ccc(C(F)(F)F)nc1)OC31CCOCC1)[C@@H](O)CC1(CC1)[C@H]2O]

Obtained by starting from (3R,6RS,9S)-9-(tert-butyldimethylsilyloxy)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]-6-yl acetate.

Mass spectrometry (ESI$^+$): m/z=505 [M+H]$^+$

HPLC (Method 1): Retention time=1.03 min.

Some examples of formulations will now be described in which the term "active substance" denotes one or more compounds according to the invention, including the salts thereof. In the case of one of the combinations with one or more additional active substances as described previously, the term "active substance" also includes the additional active substances.

Example A

Tablets Containing 100 mg of Active Substance

Composition:

1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Example B

Tablets Containing 150 mg of Active Substance

Composition:
1 tablet contains:

| active substance | 150.0 mg |
|---|---|
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

Example C

Hard Gelatine Capsules Containing 150 mg of Active Substance

Composition:

| 1 capsule contains: | |
|---|---|
| active substance | 150.0 mg |
| corn starch (dried) approx. | 180.0 mg |
| lactose (powdered) approx. | 87.0 mg |
| magnesium stearate | 3.0 mg |
| approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

Example D

Suppositories Containing 150 mg of Active Substance

Composition:

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example E

Ampoules Containing 10 mg Active Substance

Composition:

| active substance | 10.0 mg |
|---|---|
| 0.01 N hydrochloric acid q.s. | |
| double-distilled water ad | 2.0 ml |

Preparation:

The active substance is dissolved in the necessary amount of 0.01 N HCl, made isotonic with common salt, filtered sterile and transferred into 2 ml ampoules.

Example F

Ampoules Containing 50 mg of Active Substance

Composition:

| active substance | 50.0 mg |
|---|---|
| 0.01 N hydrochloric acid q.s. | |
| double-distilled water ad | 10.0 ml |

Preparation:

The active substance is dissolved in the necessary amount of 0.01 N HCl, made isotonic with common salt, filtered sterile and transferred into 10 ml ampoules.

The invention claimed is:

1. A compound of formula I

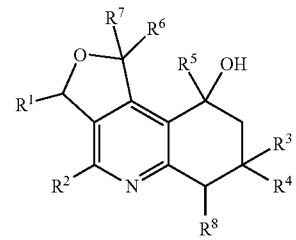

wherein
$R^1$ is a mono- or bicyclic 5- to 10-membered aryl or heteroaryl group, which heteroaryl contains 1 to 4 heteroatoms selected from the group consisting of N, O and S, and which aryl or heteroaryl may optionally be substituted by $R^9$, $R^{10}$ and/or $R^{11}$, in which
$R^9$ is hydrogen, halogen, cyano, 1-4C-alkyl, 2-4C-alkenyl, 3-6C-cycloalkyl, 1-4C-alkoxy, completely or partially fluorine-substituted 1-4C-alkyl, completely or partially fluorine-substituted 1-4C-alkoxy, pentafluorosulfanyl, cyano-1-4C-alkyl, 1-2C-alkyl-3-6C-cycloalkyl, cyano-3-6C-cycloalkyl, 1-2C-alkoxy-1-4C-alkyl, hydroxy-1-4C-alkyl or 3-(1-2C-alkyl)-oxetan-3-yl,
$R^{10}$ is hydrogen, halogen, cyano, 1-4C-alkyl, 2-4C-alkenyl, 3-6C-cycloalkyl, 1-4C-alkoxy, completely or partially fluorine-substituted 1-4C-alkyl, completely or partially fluorine-substituted 1-4C-alkoxy, cyano-1-4C-alkyl, methyl-3-6C-cycloalkyl, cyano-3-6C-cycloalkyl, methoxy-1-4C-alkyl, hydroxy-1-4C-alkyl or 3-(1-2C-alkyl)-oxetan-3-yl, $R^{11}$ is hydrogen or halogen, or $R^9$ and $R^{10}$ together and with inclusion of the carbon atoms, to which they are attached, form a 5-6C-cycloalkane ring wherein one methylene group may optionally be replaced by oxygen, which ring, for the case of 6-membered ring system, may optionally contain a double bond, and/or which ring may optionally be mono- or disubstituted by methyl, wherein, for the case that both methyl groups are connected to the same carbon, the methyl groups together with the carbon to which they are connected, may optionally form a cyclopropyl ring, $R^2$ is 1-6C-alkyl, 1-3C-perfluoroalkyl, 1-4C-alkoxy-1-4C-alkyl, or 4-7C-cycloalkyl, which 4-7C-cycloalkyl may optionally be mono- or disubstituted by fluorine, hydroxy, methoxy and/or 1-2C-alkyl and in which, for the case of 4-7C-cycloalkyl systems, one methylene group may optionally be replaced by oxygen, $R^3$ and $R^4$ together and with inclusion of the carbon atom, to which they are attached, form a 3C-cycloalkane ring, $R^5$ is hydrogen or 1-4C-alkyl, $R^6$ is 1-4C-alkyl, $R^7$ is hydrogen or 1-4C-alkyl, or $R^6$ and $R^7$ together and with inclusion of the carbon atom, to which they are attached, form a 5-7C-cycloalkane ring wherein one methylene group may optionally be replaced by oxygen, which ring may optionally contain one double bond, and/or which ring may optionally be mono- or disubstituted by fluorine, hydroxyl, 1-2C-alkoxy and/or 1-2C-alkyl, $R^8$ is hydrogen, acetoxy, propionyloxy, methoxy or hydroxy, the tautomers, the stereoisomers thereof, the mixtures thereof and the salts thereof.

2. The compound of formula I according to claim 1, wherein $R^1$ denotes 2-($R^9$)-3-($R^{10}$)-thiophen-5-yl, 5-($R^9$)-4-($R^{10}$)-thiazol-2-yl, 1-($R^{10}$)-2-($R^9$)-3-($R^{11}$)-benzene-5-yl, 1-($R^{10}$)-2-($R^9$)-4-($R^{11}$)-benzene-5-yl, 5-($R^9$)-4-($R^{10}$)-pyridine-2-yl, 2-($R^9$)-3-($R^{10}$)-pyridine-5-yl, 5-($R^9$)-3-($R^{10}$)-pyridine-2-yl, 5-($R^9$)-4-($R^{10}$)-pyrimidine-2-yl, 2-($R^9$)-pyrimidine-5-yl, 3-($R^9$)-4-($R^{10}$)-pyridazine-6-yl, 2-($R^9$)-3-($R^{10}$)-pyrazine-5-yl, 1,1-dimethyl-1,3-dihydroisobenzofuran-5-yl, 3'H-spiro[cyclopropane-1,1'-isobenzofuran]-5'-yl, 3,3-dimethyl-2,3-dihydrobenzofuran-6-yl or 2H-spiro[benzofuran-3,1'-cyclopropane]-6-yl, in which $R^9$ is hydrogen, halogen, cyano, isopropyl, isobutyl, tert.-butyl, isopropenyl, cyclopropyl, cyclobutyl, methoxy, ethoxy, isopropoxy, tert.-butoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 1-methoxy-ethan-1-yl, 2-methoxy-propan-2-yl, 1-hydroxy-ethan-1-yl, 2-hydroxy-propan-2-yl, or 3-(1-2C-alkyl)-oxetan-3-yl, $R^{10}$ is hydrogen, halogen, cyano, methyl, ethyl, isopropyl, tert.-butyl, methoxy, trifluoromethyl, trifluoromethoxy, or methoxymethyl, $R^{11}$ is hydrogen, fluorine or chlorine, $R^2$ denotes 1-5C-alkyl, trifluormethyl, pentafluorethyl, 1-3C-alkoxy-1-2C-alkyl, 1-3C-alkoxy-3C-alkyl or 4-7C-cycloalkyl, which 4-7C-cycloalkyl may optionally be mono- or disubstituted by fluorine, hydroxy, methoxy and/or methyl and in which, for the case of 4-7C-cycloalkyl, one methylene group may optionally be replaced by oxygen, $R^3$ and $R^4$ together and with inclusion of the carbon atom, to which they are attached, form a cyclopropane ring, $R^5$ denotes hydrogen or methyl, $R^6$ denotes methyl, ethyl, propyl or isopropyl and $R^7$ denotes hydrogen, methyl or ethyl, or $R^6$ and $R^7$ together and with inclusion of the carbon atom, to which they are attached, form a 5-6C-cycloalkane ring wherein one methylene group may optionally be replaced by oxygen, which ring may optionally contain one double bond, and/or which ring may optionally be mono- or disubstituted by fluorine, hydroxyl, 1-2C-alkoxy and/or 1-2C-alkyl, $R^8$ denotes hydrogen, acetoxy or hydroxy, the tautomers, the stereoisomers thereof, the mixtures thereof and the salts thereof.

3. The compound of formula I according to claim 1, wherein $R^1$ denotes 2-($R^9$)-thiophen-5-yl, 1-($R^9$)-2-($R^{10}$)-benzene-4-yl, 1-($R^9$)-3-($R^{10}$)-benzene-4-yl, 4-($R^9$)-benzene-1-yl, 3-tert.-butylphenyl, 3-trifluoromethylphenyl, 1,2,3-trifluoro-benzene-5-yl, 1,3-difluoro-benzene-5-yl, 5-($R^9$)-pyridine-2-yl, 2-($R^9$)-pyridine-5-yl, 5-($R^9$)-3-($R^{10}$)-pyridine-2-yl, 2-($R^9$)-pyrimidine-5-yl, 5-($R^9$)-4-($R^{10}$)-thiazol-2-yl, 1,1-dimethyl-1,3-dihydroisobenzofuran-5-yl or 3,3-dimethyl-2,3-dihydrobenzofuran-6-yl, in which $R^9$ is fluorine, chlorine, bromine, cyano, isopropyl, isobutyl, isopropenyl, tert.-butyl, cyclopropyl, cyclobutyl, methoxy, ethoxy, isopropoxy, tert.-butoxy, trifluoromethyl, pentafluoroethyl, difluoromethyl, 1,1-difluorethan-1-yl, trifluoromethoxy, difluoromethoxy, pentafluorosulfanyl, 2-cyano-propan-2-yl, 1-methyl-cyclopropan-1-yl, 1-methyl-cyclobutan-1-yl, 1-cyano-cyclopropan-1-yl, 1-cyano-cyclobutan-1-yl, 2-methoxy-propan-2-yl, 2-hydroxy-propan-2-yl, or 3-methyl-oxetan-3-yl, $R^{10}$ is hydrogen, methyl, cyano, methoxy, fluorine or chlorine, $R^2$ denotes ethyl, isopropyl, 2-butyl, isobutyl, tert.-butyl, 3-pentyl, cyclobutyl, cyclopentyl, cyclohexyl, methoxymethyl, 1-methoxyethyl, 2-methoxy-propan-2-yl, tetrahydrofuran-2-yl, tetrahydrofuran-3-yl, tetrahydropyran-4-yl, tetrahydropyran-3-yl or tetrahydropyran-2-yl, $R^3$ and $R^4$ together and with inclusion of the carbon atom, to which they are attached, form a cyclopropane ring, $R^5$ denotes hydrogen, $R^6$ and $R^7$ independently denote methyl or ethyl, or $R^6$ and $R^7$ together and with inclusion of the carbon atom, to which they are attached, form a cyclopentane ring, cyclopent-2-ene-1,1-diyl ring, cyclohexane ring, 4,4-difluorocyclohexan-1,1-diyl ring or tetrahydropyrane-4,4-diyl ring, $R^8$ denotes hydrogen or hydroxy, the tautomers, the stereoisomers thereof, the mixtures thereof and the salts thereof.

4. The compound of formula I according to claim 1, wherein $R^1$ denotes 4-trifluoromethylphenyl, 3-trifluoromethylphenyl, 4-(1,1-difluoro-ethan-1-yl)-phenyl, 4-methylphenyl, 4-isopropylphenyl, 4-isobutylphenyl, 4-tert.-butylphenyl, 3-tert.-butylphenyl, 4-isopropenylphenyl, 4-cyanophenyl, 4-fluorophenyl, 3,5-difluorophenyl, 4-chlorophenyl, 4-methoxyphenyl, 4-isopropoxyphenyl, 4-tert.-butoxyphenyl, 4-trifluoromethoxyphenyl, 4-pentafluorosulfanylphenyl, 4-perfluoroethyl-phenyl, 2-trifluoromethyl-pyridin-5-yl, 5-trifluoromethyl-pyridin-2-yl, 3-fluoro-4-trifluormethyl-phenyl, 2-fluoro-4-trifluoromethyl-phenyl, 3-fluoro-5-trifluoromethyl-pyridin-2-yl, 3-cyano-4-trifluoromethyl-phenyl, 3-methoxy-4-trifluoromethyl-phenyl, 4-(2-cyano-propan-2-yl)-phenyl, 4-(2-hydroxy-propan-2-yl)-phenyl, 4-cyclopropylphenyl, 4-(1-methylcyclopropyl-1-yl)-phenyl, 4-(1-cyanocyclopropyl-1-yl)-phenyl, 2-trifluoromethyl-thiophen-5-yl, 5-tert.-butyl-4-methyl-thiazol-2-yl, or 2-tert.-butyl-pyrimidin-5-yl, $R^2$ denotes ethyl, isopropyl, tert.-butyl, methoxymethyl, 1-methoxyethyl, 2-methoxy-propan-2-yl, cyclobutyl, cyclopentyl or tetrahydropyran-4-yl, $R^3$ and $R^4$ together and with inclusion of the carbon atom, to which they are attached, form a cyclopropane ring, $R^5$ denotes hydrogen, $R^6$ denotes methyl and $R^7$ denotes methyl, or $R^6$ and $R^7$ together and with inclusion of the carbon atom, to which they are attached, form a cyclopentane ring, cyclopent-2-ene-1,1-diyl ring, cyclohexane ring or tetrahydropyrane-4,4-diyl ring, $R^8$ denotes hydrogen or hydroxy, the tautomers, the stereoisomers thereof, the mixtures thereof and the salts thereof.

5. The compound of formula I according to claim 1, wherein $R^1$ denotes 4-trifluoromethylphenyl, 4-tert.-butylphenyl, 4-pentafluorosulfanylphenyl, 4-pentafluoroethylphenyl, 2-trifluoromethyl-pyridin-5-yl, 3-fluoro-4-trifluoromethyl-phenyl, 2-fluoro-4-trifluoromethyl-phenyl, 3-cyano-4-trifluoromethyl-phenyl or 3-methoxy-4-trifluoromethyl-phenyl, $R^2$ denotes isopropyl, tert.-butyl or tetrahydropyran-4-yl, $R^3$ and $R^4$ together and with inclusion of the carbon atom, to which they are attached, form a cyclopropane ring, $R^5$ denotes hydrogen, $R^6$ and $R^7$ together and with inclusion of the carbon atom, to which they are attached, form a tetrahydropyrane-4,4-diyl ring, $R^8$ denotes hydrogen or hydroxy, the tautomers, the stereoisomers thereof, the mixtures thereof and the salts thereof.

6. The compound according to claim 1, which is of formula I*

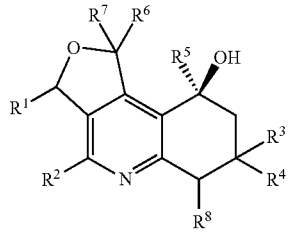

(I*)

wherein $R^1$ to $R^8$ are defined as in claim 1,
the tautomers, the mixtures thereof and the salts thereof.

7. The compound according to claim 1, which is of formula I**

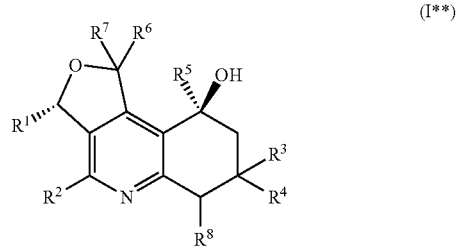

(I**)

wherein $R^1$ to $R^8$ are defined as in claim 1,
the tautomers, the mixtures thereof and the salts thereof.

8. The compound according to claim 1, which is of formula I***

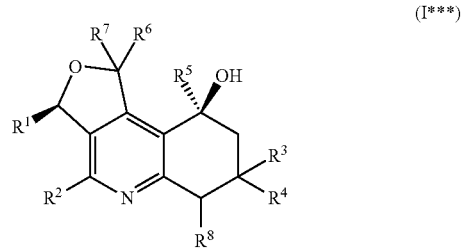

(I***)

wherein $R^1$ to $R^8$ are defined as in claim 1,
the tautomers, the mixtures thereof and the salts thereof.

9. The compound according to claim 1, which is of formula I****

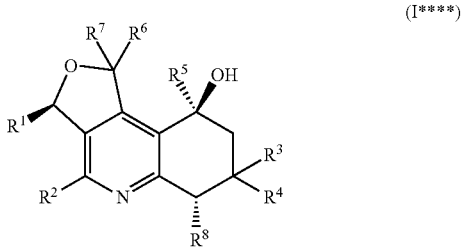

(I****)

wherein $R^1$ to $R^8$ are defined as in claim 1,
the tautomers, the mixtures thereof and the salts thereof.

10. The compound according to claim 1, which is of formula I*****

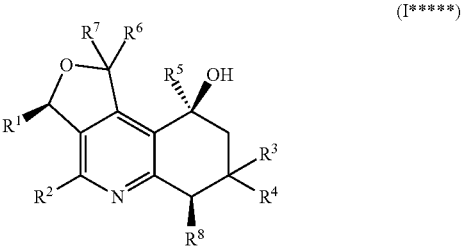

(I*****)

wherein $R^1$ to $R^8$ are defined as in claim 1,
the tautomers, the mixtures thereof and the salts thereof.

11. The compound according to claim 1, wherein:

R² denotes isopropyl,

R³ and R⁴ together and with inclusion of the carbon atom, to which they are attached, form a cyclopropane ring, R⁵ denotes hydrogen, R⁶ and R⁷ together and with inclusion of the carbon atom, to which they are attached, form a tetrahydropyrane-4,4-diyl ring, and R⁸ denotes hydrogen, the tautomers, the stereoisomers thereof, the mixtures thereof and the salts thereof.

12. The compound according to claim 1, wherein:

R² denotes isopropyl,

R³ and R⁴ together and with inclusion of the carbon atom, to which they are attached, form a cyclopropane ring, R⁵ denotes hydrogen, R⁶ and R⁷ together and with inclusion of the carbon atom, to which they are attached, form a tetrahydropyrane-4,4-diyl ring, and R⁸ denotes hydroxy, the tautomers, the stereoisomers thereof, the mixtures thereof and the salts thereof.

13. A compound according to claim 1 selected from the group consisting of:

3R,9S)-4-isopropyl-7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]-9-ol

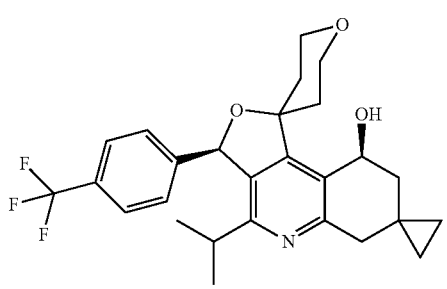

5-((3R,9S)-9-hydroxy-4-isopropyl-7,7-(ethan-1,2-diyl)-2',3',5',6,6',7,8,9-octahydro-3H-spiro[furo[3,4-c]quinoline-1,4'-pyran]-3-yl)-2-(trifluoromethyl)benzonitrile

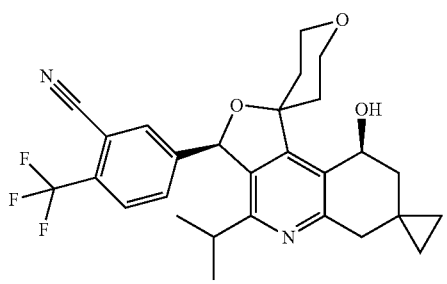 [SMILES: CC(C)c1nc2c(c3c1[C@@H](c1ccc(C(F)(F)F)c(C#N)c1)OC31CCOCC1)[C@@H](O)CC1(CC1)C2]

(3R,6R,9S)-4-isopropyl-7,7-(ethan-1,2-diyl)-3-(3-methoxy-4-(trifluoromethyl)phenyl)-2',3',5',6,6',7,8,9-octahydro-3H-spiro[furo[3,4-c]quinoline-1,4'-pyran]-6,9-diol

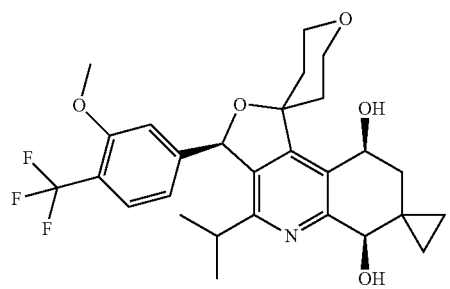 [SMILES: COc1cc([C@H]2OC3(CCOCC3)c3c2c(C(C)C)nc2c3[C@@H](O)CC3(CC3)[C@H]2O)ccc1C(F)(F)F]

(3R,9S)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]-9-ol

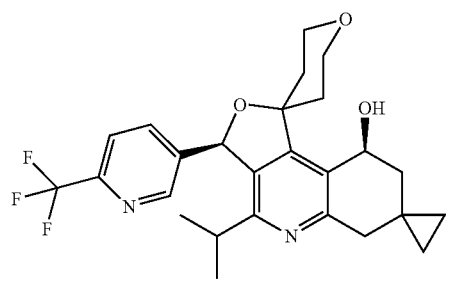

(3R,6R,9S)-4-isopropyl-7,7-(ethan-1,2-diyl)-3-(4-(trifluoromethyl)phenyl)-2',3',5',6,6',7,8,9-octahydro-3H-spiro[furo[3,4-c]quinoline-1,4'-pyran]-6,9-diol

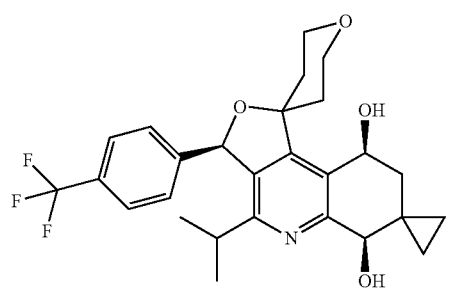

5-((3R,6R,9S)-6,9-dihydroxy-4-isopropyl-7,7-(ethan-1,2-diyl)-2',3',5',6,6',7,8,9-octahydro-3H-spiro[furo[3,4- c]quinoline-1,4'-pyran]-3-yl)-2-(trifluoromethyl)benzonitrile

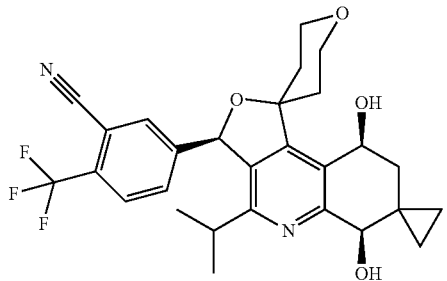 [SMILES: CC(C)c1nc2c(c3c1[C@@H](c1ccc(C(F)(F)F)c(C#N)c1)OC31CCOCC1)[C@@H](O)CC1(CC1)[C@H]2O]

(3R,6R,9S)-4-isopropyl-7,7-(ethan-1,2-diyl)-3-(3-methoxy-4-(trifluoromethyl)phenyl)-2',3',5',6,6',7,8,9-octahydro-3H-spiro[furo[3,4-c]quinoline-1,4'-pyran]-6,9-diol

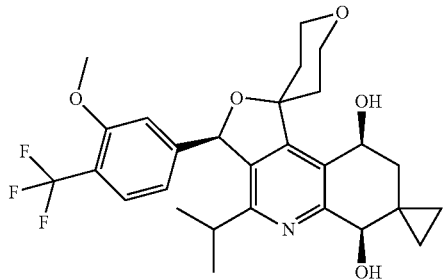 [SMILES: COc1cc([C@H]2OC3(CCOCC3)c3c2c(C(C)C)nc2c3[C@@H](O)CC3(CC3)[C@H]2O)ccc1C(F)(F)F]

and (3R,6R,9S)-4-isopropyl-7,7-(ethan-1,2-diyl)-3-(6-(trifluoromethyl)pyridin-3-yl)-2',3',5',6,6',7,8,9-octahydro-3H-spiro[furo[3,4-c]quinoline-1,4'-pyran]-6,9-diol

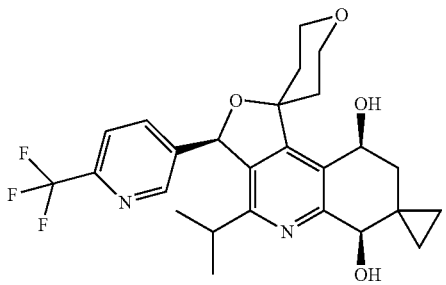

or a salt thereof.

14. A pharmaceutically acceptable salt of a compound according to claim 1 with an inorganic or organic acid or base.

15. Pharmaceutical composition comprising a compound according to claim 1 or a pharmaceutically acceptable salt with an inorganic or organic acid or base optionally together with one or more inert carriers and/or diluents.

16. A process for preparing a pharmaceutical composition comprising combining or mixing a compound of claim 1 or a pharmaceutically acceptable salt with an inorganic or organic acid or base, and one or more inert carriers and/or diluents.

* * * * *